(12) United States Patent
Friedman et al.

(10) Patent No.: US 11,052,043 B2
(45) Date of Patent: Jul. 6, 2021

(54) SUSTAINED-RELEASE INJECTABLE FORMULATION

(75) Inventors: Michael Friedman, Jerusalem (IL); Amnon Hoffman, Jerusalem (IL); Eran Lavy, Modiln (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 581 days.

(21) Appl. No.: 14/007,331

(22) PCT Filed: Mar. 28, 2012

(86) PCT No.: PCT/IL2012/050109
§ 371 (c)(1),
(2), (4) Date: Sep. 25, 2013

(87) PCT Pub. No.: WO2012/131678
PCT Pub. Date: Oct. 4, 2012

(65) Prior Publication Data
US 2014/0018323 A1     Jan. 16, 2014

Related U.S. Application Data

(60) Provisional application No. 61/468,096, filed on Mar. 28, 2011.

(51) Int. Cl.
| | |
|---|---|
| A61K 9/06 | (2006.01) |
| A61K 31/65 | (2006.01) |
| A61K 31/43 | (2006.01) |
| A61K 31/546 | (2006.01) |
| A61K 9/10 | (2006.01) |
| A61K 31/496 | (2006.01) |
| A61K 47/10 | (2017.01) |
| A61K 9/00 | (2006.01) |

(52) U.S. Cl.
CPC .............. *A61K 9/06* (2013.01); *A61K 9/0024* (2013.01); *A61K 9/10* (2013.01); *A61K 31/43* (2013.01); *A61K 31/496* (2013.01); *A61K 31/546* (2013.01); *A61K 31/65* (2013.01); *A61K 47/10* (2013.01)

(58) Field of Classification Search
CPC .......... A61K 9/06; A61K 9/0024; A61K 9/10; A61K 31/43; A61K 31/496; A61K 31/546; A61K 31/65; A61K 47/10
USPC ....................................................... 514/152
See application file for complete search history.

(56) References Cited

U.S. PATENT DOCUMENTS

| | | | |
|---|---|---|---|
| 3,740,421 A | 6/1973 | Schmolka | |
| 4,478,822 A * | 10/1984 | Haslam ................ | A61K 9/2031 424/114 |
| 5,035,891 A | 7/1991 | Runkel et al. | |
| 7,008,628 B2 | 3/2006 | Ron et al. | |
| 7,250,177 B2 | 7/2007 | Pathak et al. | |
| 2004/0247672 A1 | 12/2004 | Tracy et al. | |
| 2009/0214685 A1 | 8/2009 | Hunt | |
| 2010/0036000 A1 | 2/2010 | Lichter et al. | |

FOREIGN PATENT DOCUMENTS

| | | |
|---|---|---|
| WO | WO 98/02142 | 1/1998 |
| WO | WO 2009/105369 | 8/2009 |
| WO | WO 2012/131678 | 10/2012 |

OTHER PUBLICATIONS

International Preliminary Report on Patentability dated Oct. 10, 2013 From the International Bureau of WIPO Re. Application No. PCT/IL2012/050109.
International Search Report and the Written Opinion dated Aug. 8, 2012 From the International Searching Authority Re. Application No. PCT/IL2012/050109.
Batrakova et al. "Pluronic Block Copolymers: Evolution of Drug Delivery Concept From Inert Nancarriers to Biological Response Modifiers", Journal of Control Release, 130(2): 98-106, Sep. 10, 2008.
Communication Pursuant to Article 94(3) EPC dated Feb. 10, 2016 From the European Patent Office Re. Application No. 12720287.7.
Patent Examination Report dated May 25, 2016 From the Australian Government, IP Australia Re. Application No. 2012235634.
Examination Report dated Apr. 11, 2017 From the Australian Government, IP Australia Re. Application No. 2012235634. (4 Pages).
Communication Pursuant to Article 94(3) EPC dated Aug. 22, 2017 From the European Patent Office Re. Application No. 12720287.7. (3 Pages).
Examination Report dated Dec. 15, 2016 From the Australian Government, IP Australia Re. Application No. 2012235634. (3 Pages).

* cited by examiner

*Primary Examiner* — Yevgeny Valenrod
(74) *Attorney, Agent, or Firm* — Browdy and Neimark, PLLC

(57) ABSTRACT

A composition which comprises a biologically active agent and a polymer that exhibits a reverse thermal gelation at a physiological temperature, in a carrier, and in which the active agent is in an undissolved form is disclosed herein. Further disclosed herein are methods utilizing the compositions for treating subjects, including non-human subjects, as well as kits for preparing and using a composition. The composition is preferably a sustained release formulation, and is particularly useful for treating animals, where single-dose treatment is desired.

37 Claims, 7 Drawing Sheets

SUSTAINED-RELEASE INJECTABLE FORMULATION

RELATED APPLICATIONS

This application is a National Phase of PCT Patent Application No. PCT/IL2012/050109 having International filing date of Mar. 28, 2012, which claims the benefit of priority under 35 USC § 119(e) of U.S. Provisional Patent Application No. 61/468,096 filed on Mar. 28, 2011. The contents of the above applications are all incorporated by reference as if fully set forth herein in their entirety.

FIELD AND BACKGROUND OF THE INVENTION

The present invention, in some embodiments thereof, relates to a sustained-release formulation, and more particularly, but not exclusively, to a sustained-release formulation which is suitable, for example, for veterinary use.

Oral administration of medications, generally considered a preferred route in human medicine, is, for obvious reasons, often unfeasible in veterinary medicine, especially when large domestic animals (such as cattle) are concerned. For similar reasons, any medication requiring multiple dosing might also prove difficult, if not impractical.

Sustained release of a drug following parenteral administration is generally preferable to oral administration in veterinary medicine, for treatment of large domestic animals (such as cattle) as well as pets and other animals. Less frequent dosing is believed to improve patient safety, reduce the incidence of injection site complications and improve compliance with drug protocols. Sustained release formulations mitigate the bolus effect at the time of injection, and thus have a salutary influence on drug side effects. All of these advantages, along with the need for fewer patient caregiver visits (for practitioner-administered drugs) have a positive, downward impact on overall healthcare costs.

For certain prophylactic uses and treatments, one-time administration or infrequent administration has become a standard procedure. For example, monthly administration is available in most heartworm preventatives such as Heartguard®, Sentinel® and Interceptor medications.

Controlled release parenteral formulations may be in the form of liquids, in situ forming solids and solids [Medlicott et al., *Advanced Drug Delivery Reviews* 2004, 56:1345-1365].

Best-selling parenteral controlled release products include Posilac® milk enhancer (a liquid suspension), Micotil® antibiotic (a liquid solution), Nuflor® antibiotic (a liquid solution) and Revalor® growth enhancer (a solid implant).

Poloxamers are nonionic triblock copolymers that consist of blocks of relatively hydrophilic poly(ethylene oxide) (PEO) and relatively hydrophobic poly(propylene oxide) (PPO) arranged in A-B-A tri-block structure: PEO-PPO-PEO. Poloxamer aqueous gels are described, for example, in U.S. Pat. No. 3,740,421.

Poloxamers are used as emulsifying agents for intravenous fat emulsions, as solubilising agents to maintain clarity in elixirs and syrups, and as wetting agents for antibacterials. They may also be used in ointment or suppository bases and as tablet binders or coaters [Sweetman (Ed.), *Martindale: The Complete Drug Reference*, London: Pharmaceutical Press].

The hydrophobic-lipophilic balance (HLB) of a poloxamer may be characterized by the numbers of ethylene oxide and propylene oxide units in the copolymer. Due to their amphiphilic nature, poloxamer copolymers display surfactant properties, including an ability to interact with hydrophobic surfaces and biological membranes. In aqueous solutions at concentrations above the critical micelle concentration (CMC) these copolymers self-assemble into micelles. The diameters of poloxamer micelles usually vary from approximately 10 nm to 100 nm. The core of the micelles consists of hydrophobic PPO blocks that are separated from the aqueous exterior by a hydrated shell of PEO blocks. The core is capable of incorporating various therapeutic or diagnostic reagents [Bartrakova & Kabanov, *Journal of Controlled Release* 2008, 130:98-106].

Poloxamers are generically designated with the letter P (for "poloxamer") followed by three digits. The first two digits multiplied by 100 give the approximate molecular mass of the PPO core, and the last digit multiplied by 10 gives the percentage of PEO. For example, P407 is a poloxamer with a PPO molecular mass of 4,000 Da, and a 70% PEO content.

According to an additional designation system (used, for example, in association with Pluronic® and Lutrol® tradenames), the copolymer is designated with a letter which defines its physical form at room temperature, L for liquid, P for paste, F for flake (solid), followed by two or three digits. The first digit (or first two digits in a three-digit number) multiplied by 300, indicates the approximate molecular weight of the hydrophobic block, and the last digit multiplied by 10 gives the percentage of polyethylene oxide (PEO). For example, L61 is a liquid poloxamer with a PPO molecular mass of 1,800 Da, and a 10% PEO content, which would be designated as P181 according to the designation system described above.

U.S. Patent Application No. 20090214685 describes a thermoplastic pharmaceutical composition comprising botulinum toxin and a biocompatible poloxamer. The pharmaceutical composition can be administered as a liquid, and gels after administration into a sustained release drug delivery system from which the botulinum toxin is released over a multi-day period.

U.S. Pat. No. 7,008,628 describes a pharmaceutical composition which comprises a linear block copolymer such as a poloxamer, end-modified by a bioadhesive polymer such as polyacrylic acid. The polymer is capable of aggregating in response to an increase in temperature.

U.S. Pat. No. 7,250,177 describes gel-forming poloxamers modified with a crosslinkable group such as acrylate, which can be crosslinked to form a thermosensitive and lipophilic gel useful for drug delivery or tissue coating.

Additional background art includes U.S. Pat. No. 5,035,891, and US 2004/0247672.

SUMMARY OF THE INVENTION

Stability of the formulation and solubility of the biologically active agent therein are among the main challenges that sustained release formulations need to overcome. Solubility is a limiting property of sustained release solutions because of the limited amount of biologically active ingredient that can be dissolved in a solution while maintaining an acceptable volume of the formulation to be administered (e.g., an acceptable injection volume). The limited amount of biologically active ingredient in sustained release solution shortens the time during which the agent is released from the formulation, and increases the number of administrations needed. Often, an amount of drug or any other active agent, which is desired to achieve prolonged release, requires use of solution's volume that substantially exceeds an acceptable and/or practical volume (e.g., for injection), and thus requires multidose administration or multiple administrations per single dose (e.g., to different tissues).

The present inventors have surprisingly uncovered that a sustained release formulation which comprises an amount of an active agent that exceeds its solubility, such that at least part of the active agent is in an undissolved form (e.g., as a suspension), and which thus can comprise greater amounts of biologically active ingredient than can a solution, can be successfully prepared and practiced, thereby enabling a prolonged treatment after a single administration. This is achieved by using polymers (e.g., poloxamers) which form a gel, thereby stabilizing the suspension, and allowing for controlled release of the active agent from the gelled formulation. Poloxamers are described in the art in the context of sustained release solutions. Utilizing poloxamers in a suspension of an active agent rather than in a solution of an active agent enables utilizing the solubilizing properties of poloxamers to control release of the active ingredient via gradual dissolution of the undissolved active agent in the suspension.

The present inventors have further demonstrated that such sustained release formulations, in a form of suspension or any other form of undissolved active agent, release the active agent more effectively and controllably than do formulations in which the active agent is dissolved. Such formulations enable to use higher amounts of the active agent within a single administration, while maintaining acceptable volumes of the administered dose.

The present invention thus concerns sustained release formulations, which are suitable, inter alia, for injection, and which are based on a combination of one or more poloxamers, or any polymers that exhibit reverse thermal gelation, and a biologically active agent.

The designed formulation is thermosensitive and may transform into a gel within minutes after its injection. This unique dosage form has the ability to contain a high amount of a biologically active agent and to provide sustained release of the active agent for a prolonged time course (e.g., in the scale of weeks). These properties allow obtaining a complete treatment after a single administration (e.g., injection), unlike sustained release solutions which have a solubility limit and therefore demand multiple administrations.

The injectable formulation does not require surgical operation and may increase the duration of efficacy for a given dose and simultaneously reduce the dosing frequency.

This development may offer a viable administration modality addressing pharmacokinetic and pharmacodynamic sensibility and practicality.

According to an aspect of some embodiments of the present invention there is provided a composition comprising a biologically active agent, a polymer which exhibits reverse thermal gelation at a physiological temperature, and an aqueous carrier, wherein at least a portion of the biologically active agent is in an undissolved form.

According to some embodiments of the present invention, the biologically active agent is a therapeutically active agent.

According to some embodiments of the present invention, the undissolved form comprises solid particles.

According to some embodiments of the present invention, the polymer comprises a poloxamer.

According to some embodiments of the present invention, the poloxamer is selected from the group consisting of poloxamer 407 and poloxamer 188.

According to some embodiments of the present invention, a concentration of the poloxamer is in a range of from 2 to 50 weight percents.

According to some embodiments of the present invention, the biologically active agent is selected from the group consisting of an antibiotic, an antihelminthic and a hormone.

According to some embodiments of the present invention, a concentration of the biologically active agent is at least 3 times a solubility of the therapeutically active agent in the aqueous carrier.

According to some embodiments of the present invention, a concentration of the biologically active agent is at least 10 times a solubility of the biologically active agent in the aqueous carrier.

According to some embodiments of the present invention, a concentration of the biologically active agent is at least 3 weight percents.

According to some embodiments of the present invention, a concentration of the biologically active agent is at least 10 weight percents.

According to some embodiments of the present invention, the composition is a liquid at a temperature lower than the physiological temperature.

According to some embodiments of the present invention, the composition is a gel at a physiological temperature.

According to some embodiments of the present invention, a release of the biologically active agent from 1 ml of the gel is characterized by a half-time of at least 4 hours.

According to some embodiments of the present invention, a release of the biologically active agent from 1 ml of the gel is characterized by a half-time in a range of from 4 hours to one week.

According to some embodiments of the present invention, the composition is packaged in a packaging material and identified, in or on the packaging material, for use in the treatment of a medical condition in a subject.

According to some embodiments of the present invention, the subject is a non-human subject.

According to some embodiments of the present invention, the composition is formulated as a unit dosage form composition.

According to some embodiments of the present invention, the composition is identified for use in effecting of a biological process the biologically active agent.

According to some embodiments of the present invention, the biological process is effected by exposure to the biologically active agent for at least 2 days.

According to some embodiments of the present invention, the biologically active agent is a therapeutically active agent, the composition being for use in treating a medical condition treatable by the therapeutically active agent.

According to an aspect of some embodiments of the present invention there is provided a method of effecting a biological process in a subject in need thereof, the method comprising administering the composition as described herein to the subject, wherein the biological process is effected by exposure to the biologically active agent.

According to some embodiments of the present invention, the biological process is effected by exposure to the biologically active agent for at least 2 days.

According to some embodiments of the present invention, the biological process is associated with a medical condition, and the administering is for treating the medical condition.

According to some embodiments of the present invention, the biologically active agent is a therapeutically active agent.

According to some embodiments of the present invention, effecting the biological process results in treating a medical condition treatable by the therapeutically active agent.

According to some embodiments of the present invention, the subject is a non-human subject.

According to some embodiments of the present invention, the administering comprises subcutaneous administration.

According to some embodiments of the present invention, administering the composition to the subject is such that a serum concentration of the biologically active agent in the subject is at least a minimum effective concentration of the biologically active agent for at least 2 days.

According to an aspect of some embodiments of the present invention there is provided a kit for effecting a biological process in a subject, the kit comprising:

(a) a biologically active agent;
(b) a polymer which exhibits reverse thermal gelation at a physiological temperature; and
(c) an aqueous carrier, wherein the amounts of the biologically active agent, the polymer and the aqueous carrier are such that the amount of the biologically active agent exceeds the solubility of the biologically active agent in the amount of aqueous carrier mixed with the amount of the polymer.

According to some embodiments of the present invention, the kit of claim 30, further comprising instructions for mixing the therapeutically active agent, the polymer and the aqueous solution so as to form a composition comprising the therapeutically active agent in an undissolved form.

According to an aspect of some embodiments of the present invention there is provided a kit for effecting a biological process in a subject, the kit comprising:

(a) a biologically active agent;
(b) a polymer which exhibits reverse thermal gelation at a physiological temperature;
(c) an aqueous carrier; and,
(d) instructions for mixing the biologically active agent, the polymer and the aqueous solution in amounts and ratio so as to form a composition comprising the biologically active agent in an undissolved form.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
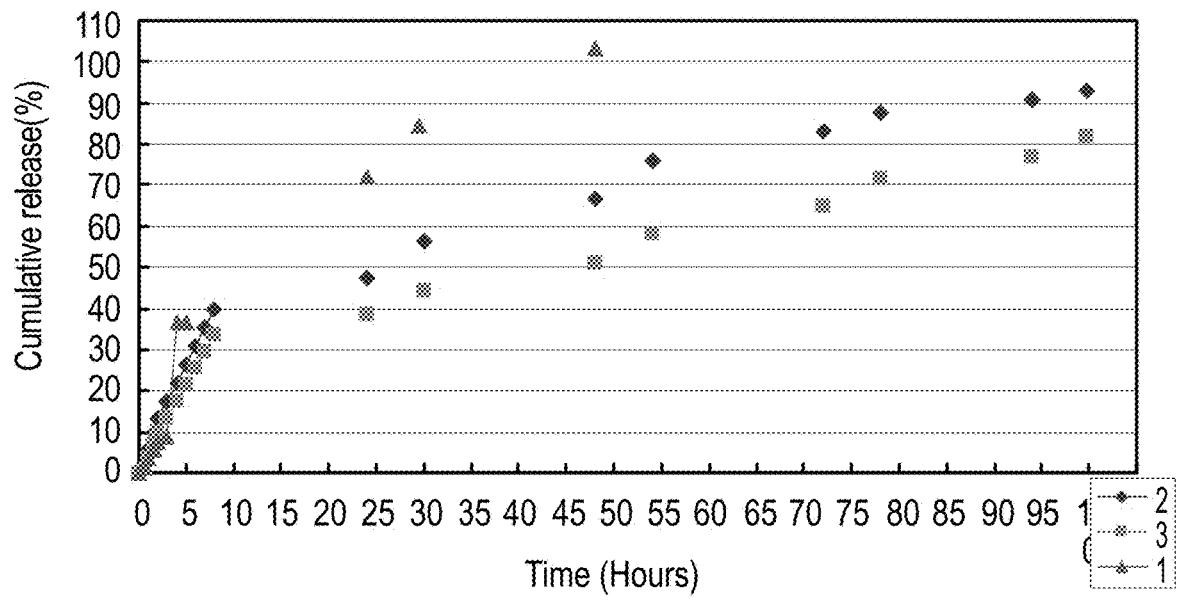
FIG. 1 presents comparative graphs showing the release of amoxicillin over time from gels prepared from solutions comprising amoxicillin.

The present invention, in some embodiments thereof, relates to a sustained-release formulation, and more particularly, but not exclusively, to a sustained-release formulation, which is suitable, for example, for veterinary use where multiple administrations are undesired.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have devised a novel sustained release formulation for drugs and other biologically active agents based on the use of polymers (e.g. poloxamers) which form a gel at physiological conditions. The sustained release of the drugs in these formulations is effected by limiting diffusion of the drug molecules through the channels present in the gel microstructure of a thermosensitive polymer as well as by controlling the erosion/dissolution of the polymer gel matrix.

The present inventors surprisingly found that when the amount of drug that is comprised in the formulation is so high that it is no longer soluble and becomes a suspension (or an emulsion), the poloxamers act to promote dissolution of the suspended particles as they are gradually released from the gel matrix. The formulation thus enables the controlled release of soluble active agent from a formulation comprising large amounts of active agents, wherein the active agent is maintained as non-soluble particles (or dispersed emulsion) in the formulation. Such formulations reduce the need for multiple dosing and thereby improve subject safety, reduce the incidence of administration complications (e.g., at an injection site) and improve compliance with drug protocols.

The present inventors have prepared a variety of sustained release formulations based on this novel concept and tested the formulations both in vitro and in vivo. The present inventors demonstrated the efficacy of the formulations on a number of different animals (e.g. goats, beagles and chicks) for a variety of different drugs (e.g. amoxicillin, doxycycline, cefdinir and enrofloxacin).

According to an aspect of some embodiments of the invention there is provided a composition comprising a biologically active agent, a polymer which exhibits reverse thermal gelation at a physiological temperature, and an aqueous carrier, wherein at least a portion of the biologically active agent is in an undissolved form in the composition, as defined herein.

As used herein the phrase "biologically active agent" refers to an agent which is accountable for the biological effect of the composition.

Exemplary biologically active agents include therapeutic, cosmetic or diagnostic agents, growth inducing agents, milk-enhancing agents, body-building agents, fat reducing agents, and additional agents, as further described herein below.

It will be appreciated that when the biologically active agent is a therapeutically active agent, the composition may be considered a pharmaceutical composition.

As used herein, a "pharmaceutical composition" refers to a preparation of the therapeutically active agent with an aqueous carrier (e.g., a pharmaceutically acceptable carrier) as described herein and other chemical components, such as a polymer as described herein, and optionally excipients, lubricants, buffering agents, antibacterial agents, bulking agents (e.g. mannitol), antioxidants (e.g., ascorbic acid or sodium bisulfite), and the like. The purpose of the pharmaceutical composition is to facilitate administration of the therapeutically active agent to a subject.

As used herein, the phrase "aqueous carrier" encompasses both water and aqueous solutions (e.g., water having one or more solutes and/or water-miscible co-solvents therein). Additional aqueous solutions include phosphate buffered saline (PBS), Hank's solution, Ringer's solution, or additional physiological salt buffers.

In some embodiments, the aqueous carrier is a pharmaceutically (or physiologically) acceptable carrier.

In some embodiments, all other components of the composition are pharmaceutically acceptable (e.g., biocompatible).

As used herein, the phrase "reverse thermal gelation" describes a property whereby a substance (e.g., an aqueous solution of a polymer) increases in viscosity upon an increase in temperature. The increase in viscosity may be, for example, conversion from a liquid state to a semisolid state (e.g., gel), conversion from a liquid state to a more viscous liquid state, or conversion from a semisolid state to a more rigid semisolid state. Herein, all such conversions are encompassed by the term "gelation".

Herein, a polymer is considered to exhibit a reverse thermal gelation at a physiological temperature when an aqueous solution of the polymer exhibits a reverse thermal gelation, as described herein, such that the solution is a gel at a physiological temperature.

A variety of polymers exhibit a reverse thermal gelation. Such polymers may be characterized by a critical gelation temperature, wherein gelation is effected at the critical gelation temperature or at temperatures above the critical gelation temperature.

Herein, "critical gelation temperature" refers to the lowest temperature at which some gelation of a material is observed (e.g., by increase in shear storage modulus).

Herein, a polymer that exhibits reverse thermal gelation is characterized by a critical gelation temperature which is selected such that an aqueous solution of the polymer is in a gelled state at a physiological temperature but not at room temperature, such that gelation may be effected in vivo.

Typically, the polymers are preferably liquid at temperatures below about 30° C., below about 25° C. or below about 20° C. and form gels at physiological temperatures.

Herein, "physiological temperature" refers to a temperature in a body of a warm-blooded animal (e.g., 37±5° C.).

Typically, reverse thermal gelation is mediated by the formation of non-covalent cross-linking (e.g., via hydrophobic interactions, ionic interactions, and/or hydrogen bonding) between molecules, wherein the degree of non-covalent cross-linking increases in response to an increase of temperature.

Herein, "non-covalent" cross-linking (formed as a result of a reverse thermal gelation) is also referred to as "physical" cross-linking or as "non-chemical cross-linking". The non-covalent cross-linking can therefore be understood as a temperature-dependent cross-linking. Typically, in aqueous solutions of RTG polymers, an endothermic sol-gel transition takes place due to an increase in entropy as temperature increases. It is suggested that the increase in entropy is caused by release of water molecules bound to at least a portion of the polymer.

Polymers exhibiting reverse thermal gelation therefore typically comprise one or more moieties which effect non-covalent cross-linking (e.g., hydrophobic moieties). The degree of gelation and the conditions (e.g., temperature) under which gelation is effected may optionally be controlled by the nature and the number of moieties which participate in non-covalent cross-linking.

In some embodiments, a polymer that exhibits reverse thermal gelation comprises from 1 and up to 100 and even 1000 moieties which participate in non-covalent cross-linking. Typically, the higher the number of such moieties, and the larger the moieties are (e.g., the higher the molecular weights are), the lower the temperature under which gelation is effected.

The polymer may comprise one or more types of moieties which effect cross-linking. These moieties may effect non-covalent cross-linking via the same intermolecular interactions (e.g., hydrophobic interactions) or via different intermolecular interactions (e.g., hydrophobic and ionic interactions).

The polymer may comprise one or more moieties which mediate a non-covalent intermolecular interaction (e.g., a hydrophobic interaction) that mediates gelation.

In some embodiments, the polymers further comprises a hydrophilic portion, which renders it soluble in aqueous solutions when cross-linking in not affected or a degree of cross-linking is low.

Thus, RTG polymers typically comprise hydrophobic and hydrophilic building blocks, whereby the gelation is mediated by the hydrophobic building blocks, and the critical gelation temperature is mediated by the number of hydrophobic moieties (e.g., hydrophobic building blocks) in the polymer.

For example, a poloxamer comprises a hydrophobic PPO moiety which mediates gelation. Similarly PCL-PEG copolymers comprise hydrophilic PEG and a relatively hydrophobic poly(ε-caprolactone) (PCL) moiety, and PEG-PAU copolymers comprise hydrophilic PEG and a hydrophobic poly(amino urethane) (PAU) moiety (e.g., a bis-1,4-(hydroxyethyl)piperazine-1,6-diisocyanato hexamethylene condensation polymer moiety).

Thus, in general, many block polymers exhibiting reverse thermal gelation may be prepared from a combination of hydrophilic and hydrophobic building blocks, whereby the type and relative portion of the hydrophobic building block can be selected such that the polymer exhibits a critical gelation temperature which is above room temperature (or above a temperature that allows a practitioner to handle the composition while is it in a liquid state or otherwise has low viscosity) and below or at physiological temperature.

Accordingly, RTG polymers that are suitable for use in the context of the present embodiments can be designed according to these guidelines so as to exhibit the desired properties, namely, to form a gel at a desired physiological temperature. All such polymers are contemplated.

By "desired physiological temperature" it is meant a body temperature of the subject being treated.

In some embodiments, the RTG polymer is such that exhibits a critical gelation temperature that ranges from about 0° C. to about 40° C., or from about 10° C. to about 40° C., or from about 20° C. to about ° C., or from about 25° C. to about ° C., or from about 30° C. to about 40° C.

In some embodiments, the RTG polymer is such that exhibits a critical gelation temperature at about 37° C.±5° C.

Exemplary polymers that exhibit reverse thermal gelation (also referred to herein and in the art as RTG polymers) at the desired physiological temperature include, but are not limited to, poloxamers, as described herein, and liquid poloxamers in particular, poly(N-isopropylacrylamide), which undergoes reverse thermal gelation at temperatures above about 32-33° C., as well as copolymers thereof (e.g., poly(N-isopropylacrylamide-co-dimethyl-γ-butyrolactone), poly(ethylene glycol)-poly(amino urethane) (PEG-PAU) block copolymers, poly(ε-caprolactone)-poly(ethylene glycol) (PCL-PEG) block copolymers (e.g., PCL-PEG-PCL), poly(methyl 2-propionamidoacrylate), and polyorganophosphazenes with PEG and hydrophobic oligopeptide side groups (which provide intermolecular hydrophobic interactions), which are gelled at temperatures of 35-43° C. (such as described, for example, in Seong et al., *Polymer* 2005, 46:5075-5081).

According to some embodiments of the invention, the polymer comprises a poloxamer.

Poloxamers (e.g., F127 poloxamer) are exemplary polymers which exhibit a reverse thermal gelation at temperatures suitable for embodiments of the present invention.

As used herein and in the art, a "poloxamer" refers to poly(ethylene oxide) (PEO)-poly(propylene oxide) (PPO) block copolymer having a PEO-PPO-PEO structure. Suitable poloxamers are commercially available, for example, as Pluronic® polymers.

As used herein and in the art, a "poloxamer" refers to poly(ethylene oxide) (PEO)-poly(propylene oxide) (PPO) block copolymer having a PEO-PPO-PEO structure.

According to some embodiments of the invention, the poloxamer is liquid at room temperature and gels at or below a physiological temperature as described herein.

Exemplary poloxamers that are suitable for use in some embodiments of the invention include, but are not limited to, poloxamer 407 (P407) and poloxamer 188 (P188).

According to some embodiments of the invention, a concentration of the poloxamer (in the pharmaceutical composition) or of any other RTG polymer as described herein is in a range of from 2 to 50 weight percents of the total weight of the composition.

The concentration of the poloxamer, or of any other RTG polymer, can be selected in accordance with a desired viscosity of the formulation, a desired gelation time and a desired release profile of the active agent from the composition, when in physiological medium. In some embodiments, when a formulation as described herein is an injectable formulation, a desired gelation time is such that substantial gelation does not occur during the injection time, yet, occurs within minutes after administration is completed. Such gelation time typically ranges from 5 minutes to 20 minutes. Those skilled in the art would readily recognize a concentration of a given RTG polymer that would exhibit a desired gelation time in a given formulation.

In some embodiments, the composition exhibits a gelation time at a physiological temperature that ranges from 0.1 to 60 minutes, or from 0.1 to 30 minutes, or from 0.1 to 20 minutes, or from 1 to 20 minutes, or from 2 to 20 minutes, or from 5 to 20 minutes, including any intermediate value therebetween. In some embodiments, a concentration of the poloxamer is selected such that the composition exhibits such gelation times.

In some embodiments, when a formulation as described herein is an injectable formulation, a desired concentration of an RTG polymer is selected such that the viscosity of the formulation does not exceed 2,000 centipoises at 20° C., or does not exceed 1,800 centipoises at 20° C., or does not exceed 1,600 centipoises at 20° C., or does not exceed 1,500 centipoises at 20° C. It is noted, however, that formulations that are intended for use in an administration route other than injection, the concentration of the polymer can be selected so as to afford a viscosity suitable for such routes of administration.

The concentration of the RTG polymer is further selected such that the polymer itself is soluble within the aqueous carrier. The solubility of the polymer depends both on the chemical composition of the RTG polymer, on the presence or absence of other components in the aqueous carrier and on the amount and chemical structure of the biologically active agent.

In some embodiments, the concentration of the RTG polymer (e.g., poloxamer) ranges from 5 to 50 weight percents, or from 5 to 40 weight percents, or from 8 to 40 weight percents, or from 10 to 40 weight percents, or from 8 to 30 weight percents, or from 10 to 30 weight percents of the total weight of the composition, including any intermediate range or value therebetween.

According to some embodiments of the invention, the composition is a liquid at a temperature lower than the physiological temperature (e.g., the composition exhibits reverse thermal gelation so as to become a gel at a physiological temperature). A liquid state is particularly suitable for facilitating administration by injection, and a composition which is a liquid at a temperature lower than the physiological temperature is suitable for being injected at a relatively convenient temperature (e.g., room temperature or a temperature close to room temperature). The liquid state can be obtained by selecting a polymer that is liquid at room temperature.

According to some embodiments of the invention, the composition is a gel at a physiological temperature.

Being formed from an aqueous solution and typically at aqueous environment (e.g., physiological environment), the gel that forms from the composition at a physiological temperature is typically a hydrogel.

As used herein and is well-known in the art, the term "hydrogel" refers to a material that comprises solid networks formed of water-soluble natural or synthetic polymer chains, and which is typically consisting primarily of water.

The gel formed from the herein disclosed composition further comprises the active agent in an undissolved form.

As discussed herein, the composition comprises a biologically active agent is an undissolved form. The undissolved form of the active agent generally refers to the solubility of the active agent when the composition is at room temperature (e.g., in a liquid state). However, embodiments in which the active agent is dissolved in the composition before gelation (e.g., at room temperature) and is in undissolved form upon gelation, are also contemplated.

Herein, the undissolved form may be a liquid (e.g., a dispersed liquid phase in an emulsion) or a solid (e.g., a dispersed solid phase in a sol).

According to some embodiments of the invention, the undissolved form comprises solid particles.

Thus, in some embodiments, the composition is in a form of a suspension, comprising the undissolved form of the biologically active agent being suspended (e.g., in a form of solid particles) in the carrier.

As used herein the term "suspension" refers to particles of the biologically active agent or aggregates of particles of the active agent suspended in the carrier liquid. In contrast, where the biologically active agent is dissolved in the carrier liquid a solution rather than a suspension is formed.

According to one embodiment, at least 5% of the biologically active agent is present in an undissolved form, at least 10% of the biologically active agent is present in an undissolved form, at least 20% of the biologically active agent is present in an undissolved form, at least 30% of the biologically active agent is present in an undissolved form, at least 40% of the biologically active agent is present in an undissolved form, at least 50% of the biologically active agent is present in an undissolved form, at least 60% of the biologically active agent is present in an undissolved form, at least 70% of the biologically active agent is present in an undissolved form, at least 80% of the biologically active agent is present in an undissolved form, at least 90% of the biologically active agent is present in an undissolved form, at least 95% of the biologically active agent is present in an undissolved form.

In some embodiments, a composition in which the active agent is in undissolved form is such that the active agent is in undissolved form at ambient conditions (e.g., room temperature and atmospheric pressure).

In some embodiments, the active agent is in undissolved form also at physiological temperature.

In some embodiments, the active agent is in undissolved form at a temperature below 40° C., or below 50° C. and even below 60° C.

Herein and in the art, a compound is considered to be in an undissolved form when its concentration in a liquid carrier is greater than its solubility constant.

A solubility constant is measured, in its simplified form, as the ratio between the concentration of a compound in its dissolved form (as a solute) and the concentration of the compound in its undissolved form (e.g., as a solid). The solubility constant of various substances is typically temperature-dependent and may depend on other factors as well.

The solubility constant represents an equilibrium state between the solute and solid states of a compound, and hence represents a saturated solution.

Determining the solubility constant can be performed by methods known in the art. For example, a mixture of a compound and a solvent is brought to equilibrium and the concentration of a species in the solution phase can be determined by chemical analysis upon separating the solid and solution phases.

According to some embodiments of the invention, a concentration of the active agent is at least 2 times a solubility of the active agent in the aqueous carrier.

According to some embodiments of the invention, a concentration of the active agent is at least 2.5 times a solubility of the active agent in the aqueous carrier.

According to some embodiments of the invention, a concentration of the active agent is at least 3 times a solubility of the active agent in the aqueous carrier.

According to some embodiments of the invention, a concentration of the active agent is at least 5 times a solubility of the active agent in the aqueous carrier.

According to some embodiments of the invention, a concentration of the active agent is at least 10 times a solubility of the active agent in the aqueous carrier. Thus, for example, the active agent is present at 1.25, 1.5, 2, 2.5, 3, 3.5, 4, 4.5, 5 times its saturation concentration in the aqueous carrier at a particular temperature (e.g. room temperature or 2-10° C.) and pressure (e.g. atmospheric pressure).

Herein, in the context of "a solubility of the active agent in the aqueous carrier" and "a solubility constant of the active agent in the aqueous carrier", the aqueous carrier refers to the carrier comprising the RTG polymer.

According to some embodiments of the invention, a concentration of the active agent is lower at least 2 times the solubility constant of the active agent in the aqueous carrier.

According to some embodiments of the invention, a concentration of the active agent is at least 2.5 times the solubility constant of the active agent in the aqueous carrier.

According to some embodiments of the invention, a concentration of the active agent is at least 3 times the solubility constant of the active agent in the aqueous carrier.

According to some embodiments of the invention, a concentration of the active agent is at least 5 times the solubility constant of the active agent in the aqueous carrier.

In some of these embodiments, the phrase "solubility constant" is as defined at room temperature.

In some of these embodiments, the phrase "solubility constant" is as defined at physiological temperature (as defined herein).

According to some embodiments of the invention, a concentration of the active agent (in the composition) is at least 3 weight percents of the total weight of the formulation.

According to some embodiments of the invention, a concentration of the active agent (in the composition) is at least 5 weight percents of the total weight of the formulation.

According to some embodiments of the invention, a concentration of the active agent (in the composition) is at least 7.5 weight percents of the total weight of the formulation.

According to some embodiments of the invention, a concentration of the active agent (in the composition) is at least 10 weight percents of the total weight of the formulation.

For example, amoxicillin may be present in the composition at 5, 10, 15, 20, 25 or 50 weight percents of the total weight of the composition.

For example, doxycycline may be present in the composition at 5, 10, 15, 20, 25, 30 or 50 weight percents of the total weight of the composition.

For example, cefdinir may be present in the composition at 5, 10, 15, 20, 25, 30 or 50 weight percents of the total weight of the composition.

The amount and type of polymer as well as the ratio of polymer to active agent to aqueous carrier in the formulation is selected such that an effective amount, as defined herein, of the biologically active agent is released in a physiological system (e.g., a bodily site or system of a subject) during a time period of at least one day, at least two days, at least 3 days, at least 4 days, at least 5 days, at least 6 days, at least 7 days, at least 8 days, at least 9 days, at least 10 days, at least 11 days, at least 12 days, at least 13 days, at least 14 days, and even for 3, 4, or more weeks.

According to some embodiments of the invention, the composition is formulated as a unit dosage form composition.

The term "unit dosage form", as used herein, describes physically discrete units, each unit containing a predetermined quantity of the biologically active agent calculated to produce the desired biologic effect, in association with the other ingredients of the composition (e.g., polymer, aqueous carrier) described herein.

Preferably, the unit dosage form comprises sufficient amount of the active agent such that it is present in the body for more than one day, more than two days, more than three days, more than 4 days, more than 5 days, more than 6 days, more than 7 days, more than 8 days, more than 9 days, more than 10 days, more than 11 days, more than 12 days, more than 13 days and even more than 14 days (e.g., 3 or more weeks) in biologically effective amounts.

Herein, a "biologically effective amount" describes an amount of the active agent that is sufficient to exhibit an intended or desired biological effect (e.g., a therapeutic effect).

A therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the biologically or therapeutically effective amount or dose can be estimated initially from in vitro and cell culture assays.

Toxicity and therapeutic efficacy of the active agents can be determined by standard pharmaceutical procedures in vitro, in cell cultures or experimental animals.

The phrases "biologically effective amount" and "therapeutically effective amount" as used herein can also be referred to as a "therapeutic window" of an active agent.

By "therapeutic window" it is meant a range of a serum concentration of an active agent at which a desired effect occurs, and which at lower concentrations of the active agent insufficient effect occurs and at higher concentrations of the active agent toxicity occurs.

Dosage amount and interval may be adjusted individually to provide plasma or brain levels of the active agent which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the nature of the biological process to be effected or the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

In some embodiments, the composition described herein is formulated such that a serum concentration of the active agent in the subject is at least a minimum effective concentration (MEC) of the active agent for at least 2 days, at least 3 days, at least 4 days, at least 5 days, at least 6 days, at least 7 days, at least 8 days, at least 9 days, at least 10 days, at least 11 days, at least 12 days, at least 13 days and even at least 14 days.

MEC values for various agents will be known to one of skill in the art. Preferably, the MEC value is calculated for the species of the subject. Optionally, an MEC can be determined from an MEC value determined in another species.

While a unit dosage form as described herein comprises an amount of the active agent that may exhibit a desired effect for a prolonged time period, in some embodiments, the unit dosage form is characterized by a volume that is suitable to be administered to the treated subject.

Such a suitable volume depends on the subject to be treated, on the route of administration and on the biologically active agent used.

For example, in case of a unit dosage form of the composition as described herein, which is an injectable formulation, the volume of the unit dosage form is no more than an acceptable injection volume of an active agent when given to an indicated subject.

Exemplary acceptable injection volumes include, but are not limited to, 4-10 ml per 100 Kg body weight for cattle and horse; 1 ml per 10 Kg body weight for pigs, sheep and goats; 0.5-1 ml per 5 Kg body weight for dogs, piglets and lambs; and 1-2 ml per hen for poultry.

Similarly, unit dosage forms for formulated for oral, rectal, ophthalmic and other routes of administration, are such that have a volume which is no more that the acceptable volume for the selected administration to an indicated subject.

Acceptable volumes for solid dosage forms for oral administration can be readily determined by a person skilled in the art of veterinary medicine and are preferably such that can be swallowed as a whole by a given animal.

Unit dosage forms as described herein, formulated for injection (injectable), can be in a form of, for example, an ampoule containing the composition, a syringe filled with the composition, and any other measured, close containers from which syringes can be filled.

Unit dosage forms as described herein, formulated for oral administration, can be in a form of, for example, sachets, pills, caplets, capsules, tablets, or discrete (e.g., separately packaged) units of granules, or suspensions of granules in water or non-aqueous media. In some embodiments, the unit dosage form comprises a composition as described herein, contained in an enteric coating (e.g., in a form of a liquid-filled capsule) which decomposes in the gastrointestinal tract, so as to expose the composition to the physiological medium and thereby form a gel as described herein. In some embodiments, the unit dosage form comprises a measured liquid formulation such as a suspension and/or a syrup.

Unit dosage forms as described herein, formulated for topical administration, can be in a form of, for example, a patch, a swab, a pledget, a pad, a tincture, a metered-dose aerosol, and the like.

According to some embodiments of the invention, a release of the active agent from 1 ml of the gel described herein is characterized by a half-time of at least 2 hours, optionally 4 hours, optionally 6 hours, optionally 8 hours, optionally 12 hours, optionally 24 hours. Optionally, the release is measured according to procedures exemplified herein.

The term "half-life" as used herein refers to the time it takes for the serum concentration of the active agent to reduce by 50%, in vivo, for example due to degradation of the active agent and/or clearance and/or sequestration by natural mechanisms.

According to some embodiments of the invention, a release of the active agent from 1 ml of the gel described herein is characterized by a half-time in a range of from 4 hours to one week.

The time period during which a dosage form continuously releases a an effective amount of the biologically active agent may be determined using the U.S. Pharmacopeia (USP) basket method I (e.g., rotation speed 100 rotations per minute, dissolution medium 900 ml of USP buffer pH 2, at 37° C.). Alternatively, determination can be made by simply placing the dosage form in distilled water or a buffer and measuring continuously the amount of the active agent in the solution.

The compositions of embodiments of the present invention may also comprise other components (i.e., in addition to the above-described components) and excipients which will improve administration of a compound to the subject.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Compositions of the present embodiments may be manufactured by processes well known in the art, e.g., by means of conventional mixing, dissolving, granulating, dragee-making, levigating, emulsifying, encapsulating, entrapping or lyophilizing processes. Proper formulation is dependent upon the route of administration chosen.

In some embodiments, the composition is an injectable composition.

For injection, the active ingredients of the composition may be formulated in the composition of the present invention, preferably in the presence of physiologically compatible buffers such as Hank's solution, Ringer's solution, or physiological salt buffer.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. For parenteral administration, the active ingredients may be combined with the composition of the present invention either in the presence or absence of other solvents, as long as the solubility of the active agent is as defined herein (as being in undissolved form).

The pharmaceutical composition described herein may be formulated for intravenous administration.

The pharmaceutical composition described herein may be formulated for subcutaneous administration.

For transmucosal administration, other penetrants appropriate to the barrier to be permeated may be used in the formulation. Such penetrants are generally known in the art.

For oral administration, the composition can be formulated readily by combining the active compounds with the carrier composition of the present invention. The carrier composition preferably enables the pharmaceutical composition to be formulated as dragees, capsules, liquids, gels, syrups, slurries, suspensions, and the like, for oral ingestion by a subject.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol.

For buccal administration, the compositions may take the form of tablets or lozenges formulated in conventional manner.

The compositions of the present invention may be formulated for topical administration. Examples of topical formulations include, but are not limited to a gel, a cream, an ointment, a paste, a lotion, a milk, a suspension, an aerosol, a spray, a foam and a serum.

The composition of the present invention may also be formulated in rectal compositions such as suppositories or retention enemas, using, e.g., conventional suppository bases such as cocoa butter or other glycerides.

According to some embodiments of the invention, the composition (or unit dosage form) is packaged in a packaging material and identified, optionally in print, in or on the packaging material, for use in effecting a biological process (e.g., treatment of a medical condition) in a subject.

According to another aspect of embodiments of the invention, there is provided a kit, the kit comprising:
(a) a biologically active agent as defined herein;
(b) a polymer which exhibits reverse thermal gelation at a physiological temperature, as defined herein; and
(c) an aqueous carrier, as defined herein.

In some embodiments, an amount of the biologically active agent, the polymer and the aqueous carrier within the kit are such that the amount of the biologically active agent exceeds the solubility of the biologically active agent in the amount of aqueous carrier, optionally when mixed with the amount of the polymer.

Such a kit can be used for forming the composition as described herein and can be identified for use in effecting a biological process.

The kit may include instructions as to how to prepare the composition (e.g. the amounts of each component to be added, the temperature at which they should be added and/or stored, the time of incubation and the order in which they should be added) such that the agent is in an undissolved form when formulated (e.g., as described herein). The kit may further include instructions as to how to prepare a composition in a liquid form (e.g., by preparing and maintaining the composition below the gelation temperature of the polymer).

The kit may further comprise instructions how to administer the composition and may optionally comprise devices or means for administering the composition. For example, the kit may comprise measuring devices such as spoons, measured receptacles, syringes, etc., depending on the intended route of administration. Alternatively, the kit may comprise a patch or bandage onto which the composition is to be deposited for topical application.

The components of the kit may be present in pre-measured amounts, as unit dosage units (e.g. in ampoules, syringes or any other measured vials) either separately or in combination. Thus, for example the active agent may be comprised in a first container in an amount that is suitable for a single administration (e.g., a unit dosage form, as defined herein). The active agent may be present in a powder form, a lyophilized form, or in a particulate form, or, alternatively, in a liquid form (depending, for example, on its state at room temperature).

The aqueous carrier may be in a separate container or the same container as the active agent. Optionally, the polymer is present in the kit in a separate container than the active agent and/or the carrier. Optionally, the active agent is present in the kit in a separate container than the carrier and the polymer.

Further optionally, all components are packaged within the same container.

In certain embodiments, the kit of embodiments of the present invention can be manufactured in a ready-to-use format and packaged in a medically acceptable container such as a syringe. The composition is contained within the syringe barrel, and is transferable from the barrel by actuating a plunger. Compositions for use in other routes of administration can be provided within the kit in a suitable form (e.g., as a patch or bandage or metered-dose aerosol containing the composition for topical application or within a container configured for oral administration, etc.)

The present embodiments further contemplate kits where at least one of the agents is present in multi-dose amounts (e.g. as a stock solution). In this case, the kit may also comprise a measuring device, such as a syringe or spoon or a measured vial or other receptacle.

The kit may also comprise the active agent already formulated in its carrier and polymer, which is placed in a single container, and labeled for treatment of an indicated condition, as further detailed herein.

According to some embodiments of the invention, the kit or the composition (including unit dosage form composition) as described herein is identified for use in effecting a biological process effected by the biologically active agent. Examples of such processes and active agents are provided hereinafter.

According to some embodiments of the invention, the kit or the composition as described herein is identified for use in the treatment of a medical condition treatable by the therapeutically active agent. Examples of medical conditions and therapeutically active agents are provided hereinafter.

The components described herein above, whether in a form of a composition or a kit may, if desired, be presented in a pack or dispenser device, such as an FDA-approved kit, which may contain one or more unit dosage forms containing the active agent. The pack may, for example, comprise metal or plastic foil, such as a blister pack. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions and kits as described herein may also be prepared, placed in an appropriate container, and labeled for effective a biological process (e.g., for treatment of an indicated disease or disorder), as is detailed herein.

According to an aspect of some embodiments of the invention, there is provided a method of effecting a biological process in a subject in need thereof, the method comprising administering to the subject the composition as described herein, wherein said biological process is effected by exposure to said biologically active agent.

Further according to an aspect of some embodiments of the present invention there is provided a use of a composition as described herein in the manufacture of a product or article for effecting a biological process, as described herein.

Exemplary biological processes that may be effected using the compositions and/or kits described herein include, but are not limited to, milk enhancement, fat reduction, muscle enhancement, growth enhancement, treatment of a disease or disorder, disease prevention (prophylaxis), tissue and/or bone regeneration, enhancement of fertility and reduction of fertility.

Examples of structural classes of agents which are suitable for inclusion in the compositions described herein include, but are not limited to, inorganic or organic compounds; small molecules (i.e., less than 1000 Daltons) or large molecules (i.e., above 1000 Daltons); biomolecules (e.g. proteinaceous molecules, including, but not limited to, protein (e.g. enzymes or hormones) peptide, polypeptide, post-translationally modified protein, antibodies etc.) or nucleic acid molecules (e.g. double-stranded DNA, single-stranded DNA, double-stranded RNA, single-stranded RNA, or triple helix nucleic acid molecules), cells (e.g., stem cells) or chemicals. The agents may be cellular agents derived from any known organism (including, but not limited to, animals, plants, bacteria, fungi, protista or viruses) or from a library of synthetic molecules.

Exemplary types of active agents include, but are not limited to peptides, neuropeptides, hormones (including for example growth hormone, oestrone, oestadiol-17β, testosterone and progesterone), vitamins, proteins including growth factors (e.g. insulin-like growth factor) and growth factor receptors (e.g. epidermal growth factor receptors).

According to some embodiments of the present invention, the active agent is a therapeutically active agent (e.g., a drug).

Non-limiting examples of therapeutically active agents that are suitable for use in this context of the present invention include antimicrobial and antibiotic agents, anti-fungal agents, anti-protozoal agents, birth control agents, fertility agents, anti-parasitic agents (e.g., anti-helminthic agents), hormones, beta blockers (e.g., metoprolol, atenolol, bisoprolol, propranolol), calcium channel blockers (e.g., verapamil), anti-diabetic agents (e.g., glipizide), anti-epileptic agents, anti-depressant agents, antihypertensive agents, analgesics and anti-inflammatory agents (e.g., non-steroidal anti-inflammatory drugs, COX-2 inhibitors, glucocorticosteroids, opioid analgesics), and anti-Parkinsonian agents.

Non-limiting examples of antimicrobial and antibiotic therapeutically active agents that are suitable for use in this context of the present invention include, without limitation, mandelic acid, 2,4-dichlorobenzenemethanol, 4-[bis(ethylthio)methyl]-2-methoxyphenol, 4-epi-tetracycline, 4-hexylresorcinol, 5,12-dihydro-5,7,12,14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammoniumsulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, azanidazole, azidamfenicol, azidocillin, azithromycin, azlocillin, aztreonam, bacampicillin, bacitracin, bacitracin zinc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefmenoxime, cefmetazole, cefmetazole sodium, cefminox, cefminox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibrompropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin magnesium, flucloxacillin sodium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin c1a, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin A5, leucomycin A6, leucomycin A7, leucomycin A8, leucomycin A9, levofloxacin, lincomycin, lincomycin hydrochloride, linezolid, liranaftate, 1-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin c, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin a, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, ornidazole, orthophenylphenol, oxacillin, oxacillin sodium, oxiconazole, oxiconazole nitrate, oxoferin, oxolinic acid, oxychlorosene, oxytetracycline, oxytetracycline calcium, oxytetracycline hydrochloride, panipenem, paromomycin, paromomycin sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium-tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin B1, polynoxylin, povidone-iodine, propamidin, propenidazole, propicillin, propicillin potassium, propionic acid, prothionamide, protiofate, pyrazinamide, pyrimethamine, pyrithion, pyrrolnitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin b, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarbamide, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfonamides, sultamicillin, sultamicillin tosilate, tacrolimus, talampicillin hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, thiomersal, thiram, thymol, tibezonium iodide, ticarcillin, ticarcillin-clavulanic acid mixture, ticarcillin disodium, ticarcillin monosodium, tilbroquinol, tilmicosin, tinidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibornol and zinc undecylenate.

Non-limiting examples of antifungal agents that are suitable for use in this context of the present invention include, without limitation, amphotericin B, caspofungin, fluconazole, flycytosine, itraconazole, ketoconazole, posaconazole, terbinafine, and voriconazole.

Non-limiting examples of anti-protozoal agents that are suitable for use in this context of the present invention include, without limitation, albendazole, amphotericin, atovaquone, azithromycin, clindamycin, diminazen, furazolidone, imidocarb, mebendazole, metronidazole, miltefosine, niazoxanide, paromomycin, pentavalent antimonials (e.g., meglumine antimoniate, sodium stibogluconate), pyrimethamine, quinacrine, quinine, spiramycin, sulfonamides (e.g., sulfadiazine), tinidazole, trypan blue, and zoalene.

Non-limiting examples of anti-parasitic agents (e.g., anti-helminthic agents) that are suitable for use in this context of the present invention include, without limitation, abamectin, albendazole, diethylcarbamazine, emodepside, flubendazole, fenbendazole, ivermectin, levamisole, mebendazole, melarsomine, milbemycin, monepantel, moxidectin, niclosamide, praziquantel, pyrantel pamoate, suramin, thiabendazole, thiacetarsamide, and triclabendazole.

According to some embodiments of the invention, the therapeutically active agent is an antibiotic, an antihelminthic and/or a hormone.

Examples of diagnostic agents which can be used in accordance with the present invention include the x-ray imaging agents, fluorescent imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(ace-tamido)-2,4,6-triiodobenzoate; ethyl-2-(3,5-bis(acetamido)-2,4,6-triiodo-b-enzoyloxy) butyrate (WIN 16318); ethyl diatrizoxyacetate (WIN 12901); ethyl 2-(3,5-bis(acetamido)-2,4,6-triiodobenzoyloxy) propionate (WIN 16923); N-ethyl 2-(3,5-bis(acetamido)-2,4,6-triiodobenzoyloxy) acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyl-oxy malonate (WIN 67721); ethyl 2-(3,5-bis(acetamido)-2,4,6-triiodobenzoyloxy) phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Other contrast media include, but are not limited to, magnetic resonance imaging aids such as gadolinium chelates, or other paramagnetic contrast agents. Examples of such compounds are gadopentetate dimeglumine (Magnevist®) and gadoteridol (Prohance®). Patent Application No. 20010001279 describes liposome comprising microbubbles which can be used as ultrasound contrast agents. Thus, diagnostic contrast agents can also be used in corporation with the present invention for aiding in ultrasound imaging of the brain.

Labeled antibodies may also be used as diagnostic agents in accordance with this aspect of the present invention. Use of labeled antibodies is particularly important for diagnosing diseases such as Alzheimer's where presence of specific proteins (e.g., (3 amyloid protein) are indicative of the disease.

A description of classes of therapeutic agents and diagnostic agents and a listing of species within each class can be found in Martindale, The Extra Pharmacopoeia, Twenty ninth Edition, The Pharmaceutical Press, London, 1989 which is incorporated herein by reference and made a part hereof. The therapeutic agents and diagnostic agents are commercially available and/or can be prepared by techniques known in the art.

As mentioned above, the composition may also be used for sustained release of cosmetic agent. A cosmetic agent of the present invention can be, for example, an anti-wrinkling agent, an anti-acne agent, a vitamin, a skin peel agent, a hair follicle stimulating agent or a hair follicle suppressing agent. Examples of cosmetic agents include, but are not limited to, retinoic acid and its derivatives, salicylic acid and derivatives thereof, sulfur-containing D and L amino acids and their derivatives and salts, particularly the N-acetyl derivatives, alpha-hydroxy acids, e.g., glycolic acid, and lactic acid, phytic acid, lipoic acid, collagen and many other agents which are known in the art.

According an aspect of some embodiments of the invention, there is provided a method of effecting a biological process in a subject in need thereof, the method comprising administering a composition as described herein to the subject, wherein the condition is effected by exposure to the active agent.

In some embodiments, the biological process is associated with a medical condition, and in some embodiments, effecting the biological process results in treating a medical condition.

According to an aspect of some embodiments of the invention, there is provided a method of treating a medical condition in a subject in need thereof, the method comprising administering a pharmaceutical composition as described herein to the subject, wherein the medical condition is treatable by exposure to the therapeutically active agent.

Further according to an aspect of some embodiments of the present invention there is provided a use of a composition as described herein in the manufacture of a medicament for treating a medical condition, as described herein.

The present invention contemplates treatment of any medical condition, including but not limited to, bacterial infections, viral infections, fungal infections, proliferative disorders (e.g. cancer), angiogenesis-related disorders, immune disorders, neurodegenerative disorders, movement disorders, muscular disorders, cardiac disorders and metabolic disorders, and any other diseases and disorders that are treatable by the therapeutically active agent used, either directly or indirectly, and optionally in combination with other active agents.

According to some embodiments of the invention, the subject is a non-human subject, preferably a warm-blooded animal (e.g., a mammal including birds, cows, horses, goat, sheep, pigs, dogs, cats, chickens and turkeys).

According to some embodiments of the invention, administration of the composition is effected every day, every 2 days, every 3 days, every 4 days, every 5 days, every 6 days, every 7 days, every 8 days, every 9 days, every 10 days, every 11 days, every 12 days, every 13 days, and every 14.

In some embodiments, the method is effected by a single administration of the composition.

In some embodiments, the method is effected by from one to 20 administrations, or from 1 to 10 administrations or from 1 to 5 administrations or from 1 to 4 administrations or from 1 to 3 administrations or by 1 or 2 administrations.

The administrations can be effected at the above-indicated time intervals and/or concomitantly, such that during one administration, the composition is administered once, twice or more, preferably each administration being effected via a different route of administration or at different tissues.

It will be appreciated that when the composition comprises a therapeutic agent which is used to treat a particular disease, the composition is typically administered during the course of the disease (and/or following the disease for a particular length of time). The composition may also comprise a therapeutic agent which is used to prevent a particular disease and as such is not limited to a particular time frame.

Compositions of the present invention may be administered to the subjects (e.g. mammal) using various routes of administration. Examples of routes of administration include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, periodontal, intra-reticular, or intraocular injections.

Alternately, one may administer the composition in a local rather than systemic manner, for example, via injection of the pharmaceutical composition directly into a tissue region of a patient.

According to some embodiments of the invention, administering the pharmaceutical composition comprises subcutaneous administration.

It is expected that during the life of a patent maturing from this application many relevant biologically active agents will be developed and the scope of the term "biologically active agent" is intended to include all such new agents a priori.

It is expected that during the life of a patent maturing from this application many relevant polymers exhibiting reverse thermal gelation properties as described herein will be developed and the scope of the phrase "a polymer which exhibits reverse thermal gelation at a physiological temperature" is intended to include all such new technologies a priori.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "about" describes ±10%. Hereinthroughout, the term "composition" is also referred to as "formulation" or "sustained-release formulation".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Numeral values described herein may have 1, 2 or 3 decimal digits but should not be regarded as limited to the indicated number of decimal digits. For example, a numeral value having 2 decimal digits is to be interpreted as encompassing also the closest numeral value having 1 or no decimal digit.

Example 1

Gelation of Amoxicillin Suspensions and Amoxicillin Release at 37° C.

Liquid formulations were prepared from the poloxamer P407 (Lutrol® F127, BASF, Germany), poloxamer P188 (Lutrol® F68, BASF, Germany), phosphate buffer (pH 6.8, according to U.S. Pharmacopeia), and amoxicillin trihydrate.

As shown in Table 1 below, amoxicillin solutions (Formulations 1-3) were prepared from 9% poloxamer P407, 25% poloxamer P188, and low concentrations (0.5-1.96%) of amoxicillin.

As further shown therein, amoxicillin suspensions (Formulations 4-6) were prepared from 12-15% poloxamer P407 and high concentrations (9.7-25%) amoxicillin.

TABLE 1

Composition of prepared amoxicillin formulations

| Formulation no. | Ingredients | Amount by weight (grams) | Amount by % (% w/w) |
|---|---|---|---|
| 1 (solution) | Poloxamer P407 | 1.79 | 9 |
| | Poloxamer P188 | 4.975 | 25 |
| | Phosphate buffer | 13.134 | 66 |
| | Amoxicillin | 0.0995 | 0.5 |
| 2 (solution) | Poloxamer P407 | 1.782 | 9 |
| | Poloxamer P188 | 4.95 | 25 |
| | Phosphate buffer | 13.06 | 66 |
| | Amoxicillin | 0.198 | 0.99 |
| 3 (solution) | Poloxamer P407 | 1.765 | 9 |

TABLE 1-continued

Composition of prepared amoxicillin formulations

| Formulation no. | Ingredients | Amount by weight (grams) | Amount by % (% w/w) |
|---|---|---|---|
| (solution) | Poloxamer P188 | 4.902 | 25 |
| | Phosphate buffer | 12.941 | 66 |
| | Amoxicillin | 0.39 | 1.96 |
| 4 (suspension) | Poloxamer P407 | 2.79 | 14 |
| | Phosphate buffer | 15.258 | 76.29 |
| | Amoxicillin | 1.945 | 9.7 |
| 5 (suspension) | Poloxamer P407 | 2.899 | 15 |
| | Phosphate buffer | 15.144 | 75.72 |
| | Amoxicillin | 1.957 | 9.8 |
| 6 (suspension) | Poloxamer P407 | 2.4 | 12 |
| | Phosphate buffer | 12.6 | 63 |
| | Amoxicillin | 5 | 25 |

The poloxamer and buffer were mixed to form a liquid suspension or solution, and transferred to a temperature of 4° C. The active ingredient (amoxicillin) was then added. The suspension (or solution) was returned to room temperature for 30 minutes before testing.

In order to test gelation, test tubes were kept at a temperature of 37° C. The tested suspension (or solution) was then added to a test tube. Gelation was determined by visual observation over time.

Formulation 2 (a solution) gelled after 12 minutes at 37° C.

Formulation 3 (a solution) gelled after 14 minutes at 37° C.

Formulation 4 (a suspension) gelled after 9 minutes at 37° C.

Formulation 5 (a suspension) gelled after 2 minutes at 37° C.

Formulation 6 (a suspension) gelled after 5 minutes at 37° C.

These results show that the suspensions undergo gelation when exposed to a physiological temperature, and that the suspensions gel more rapidly than the solutions.

In order to test release of amoxicillin from the gelled formulations, test tubes containing a 2 or 5 grams of a gelled amoxicillin formulation described hereinabove were incubated at a temperature of 37° C. Phosphate buffer was added at a volume equal to the volume of the gel (2 or 5 ml). The buffer was then removed from the different test tubes at different pre-determined times.

The amount of released amoxicillin was determined by measuring absorption at 272 nm, using a UVIKON 933 spectrophotometer, and comparing results with a calibration curve determined by measuring solutions with known concentrations of amoxicillin.

Figure 2:
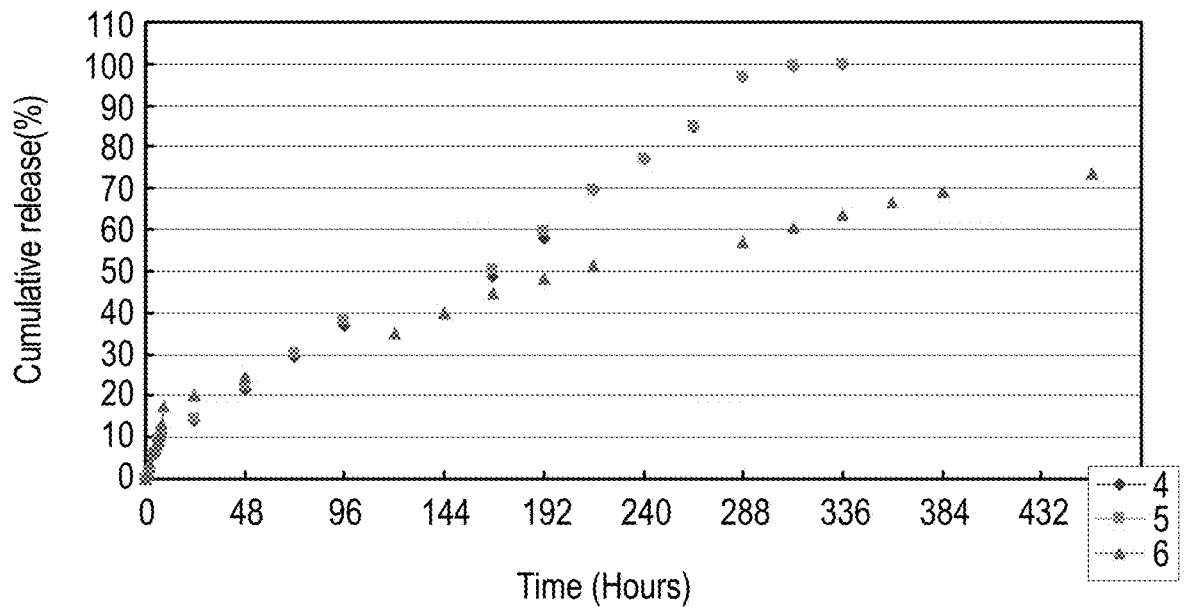
FIG. 2 presents comparative graphs showing the release of amoxicillin over time from gels prepared from suspensions comprising amoxicillin, according to exemplary embodiments of the invention.
Figure 3A:
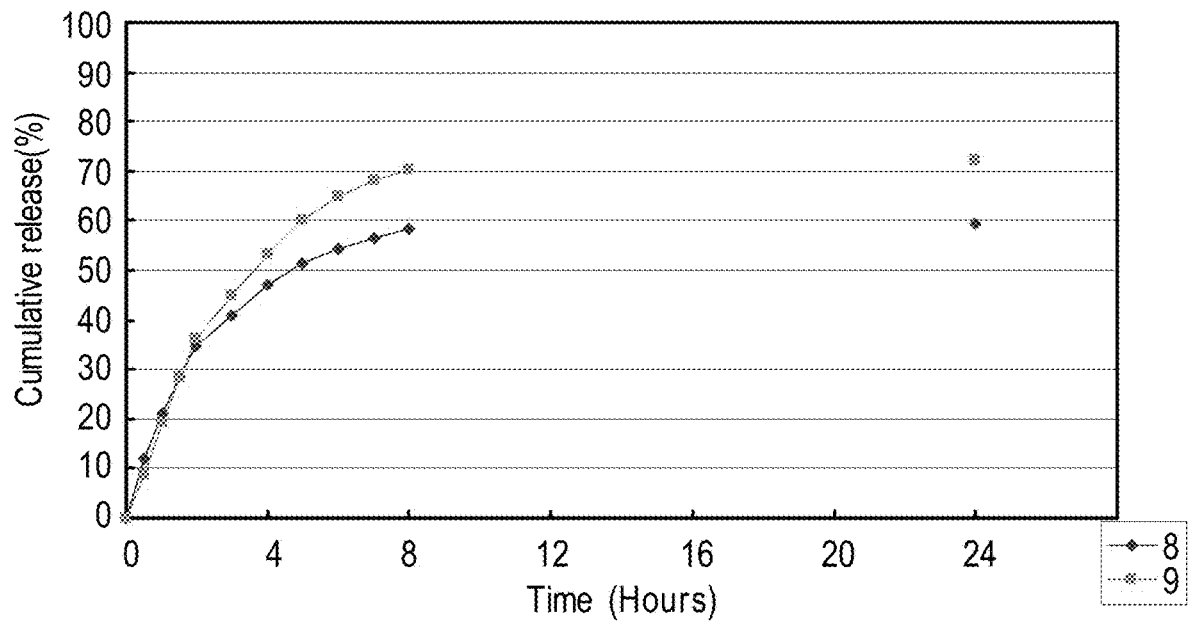
FIGS. 3A and 3B present comparative graphs showing the release of doxycycline over time from gels prepared from solutions comprising doxycycline (FIGS. 3A and 3B show results for the same formulations in different experiments)
Figure 3B:
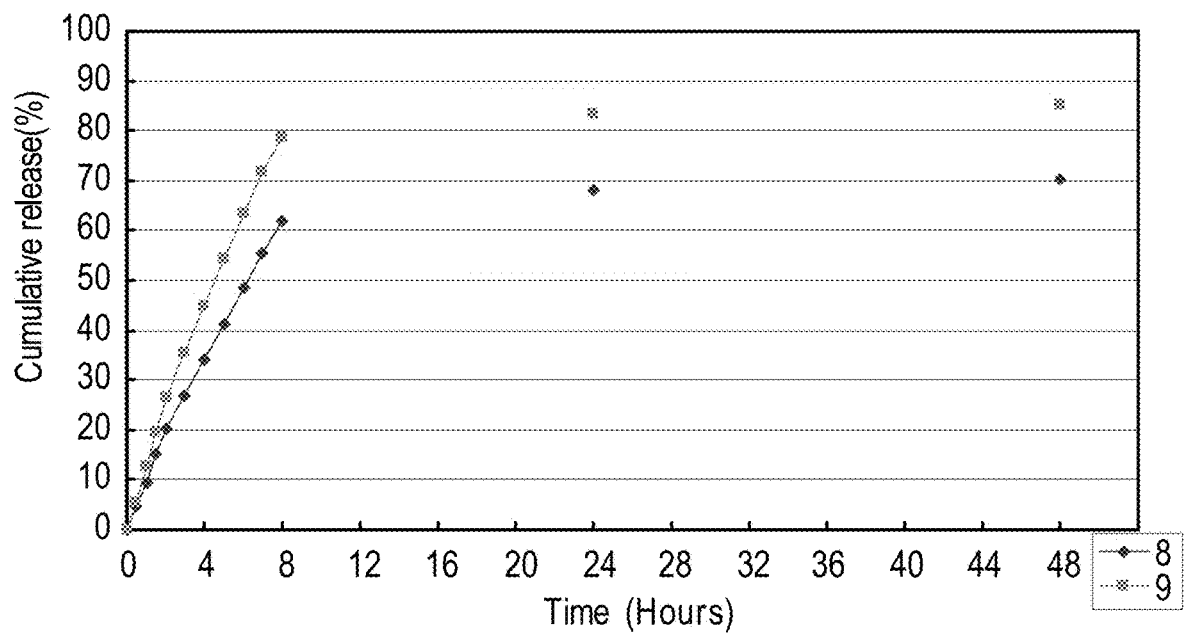
Figure 4A:
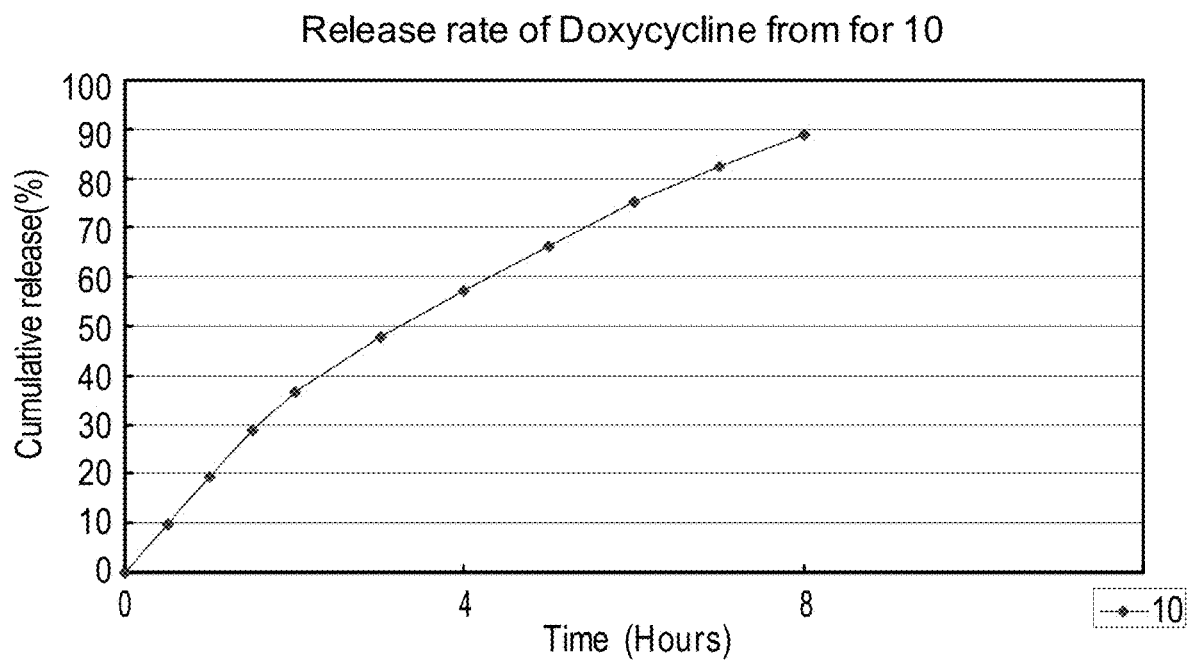
FIGS. 4A and 4B present graphs showing the release of doxycycline over time from gels prepared from suspensions comprising doxycycline, according to exemplary embodiments of the invention (FIGS. 4A and 4B show results for different formulations)
Figure 4B:
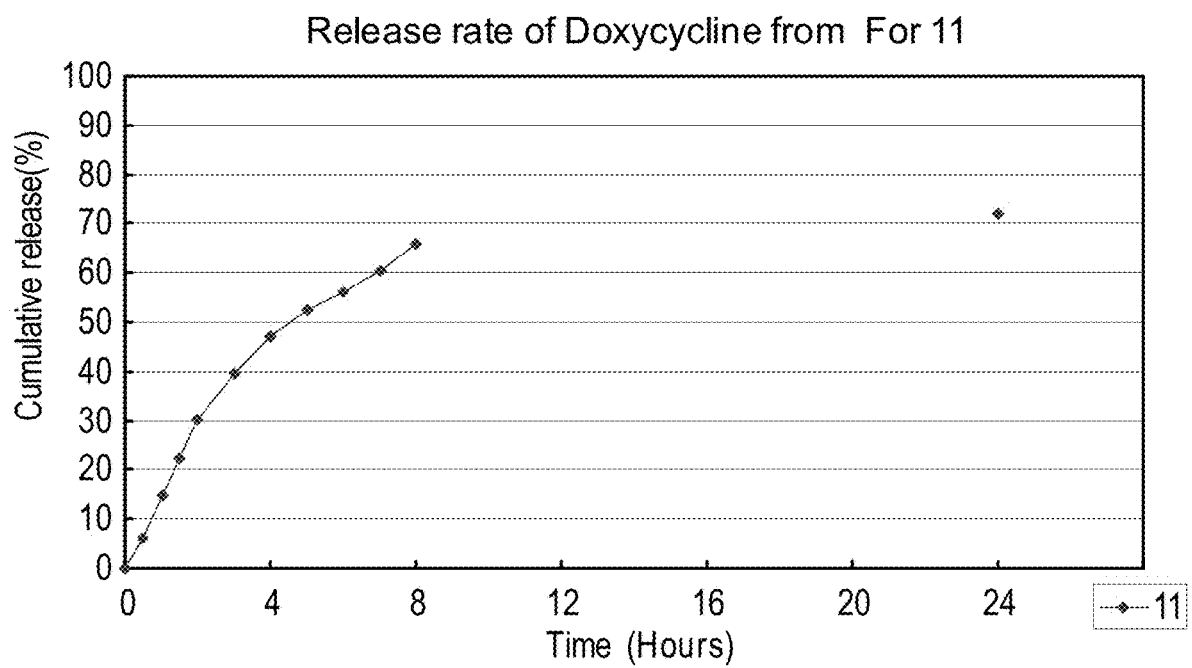

As shown in FIGS. 1 and 2, the gels prepared from suspensions (FIG. 2) released amoxicillin more gradually than did the gels prepared from solutions (FIG. 1).

In addition, the total amount of amoxicillin released from the gelled suspensions was considerably higher than that released from the gelled solutions, as the suspensions comprised a considerably higher concentration of amoxicillin.

Example 2

Gelation of Doxycycline Suspensions and Doxycycline Release at 37° C.

Liquid formulations were prepared from the poloxamer P407, poloxamer P188, water, and doxycycline.

As shown in Table 2 below, doxycycline solutions (Formulations 7-9) were prepared from poloxamer P407 or a mixture of poloxamers P407 and P188, and a relatively low concentration (9.09%) of doxycycline.

As further shown therein, doxycycline suspensions (Formulations 10-11) were prepared from about 22% poloxamer P407 and relatively high concentrations (25.8-30%) of doxycycline.

TABLE 2

Composition of prepared doxycycline formulations

| Formulation no. | Ingredients | Amount by weight (grams) | Amount by % (% w/w) |
|---|---|---|---|
| 7 (solution) | Poloxamer P407 | 2.73 | 13.64 |
| | Poloxamer P188 | 5.455 | 27.27 |
| | Water | 10 | 50 |
| | Doxycycline | 1.82 | 9.09 |
| 8 (solution) | Poloxamer P407 | 4.55 | 22.73 |
| | Water | 13.64 | 68.18 |
| | Doxycycline | 1.82 | 9.09 |
| 9 (solution) | Poloxamer P407 | 3.64 | 18.18 |
| | Water | 14.55 | 72.73 |
| | Doxycycline | 1.82 | 9.09 |
| 10 (suspension) | Poloxamer P407 | 4.53 | 22.67 |
| | Water | 9.47 | 47.33 |
| | Doxycycline | 6 | 30 |
| 11 (suspension) | Poloxamer P407 | 4.39 | 21.93 |
| | Water | 10.45 | 52.26 |
| | Doxycycline | 5.16 | 25.81 |

The poloxamer, water and active ingredient (doxycycline) were mixed using the procedures described in Example 1. Gelation of the obtained suspension or solution was tested as described in Example 1.

Formulation 7 (a solution) gelled after 20 minutes at 37° C.

Formulation 8 (a solution) gelled after 2 minutes at 37° C.

Formulation 9 (a solution) gelled after 5 to 10 minutes at 37° C.

Formulation 10 (a suspension) gelled after 1.5 to 2.5 minutes at 37° C.

These results indicate that the suspensions undergo gelation when exposed to a physiological temperature, and that the suspensions gel at least as rapidly as do the solutions.

In order to test release of doxycycline from the gelled formulations, test tubes containing 1 ml of a gelled doxycycline formulation described hereinabove were incubated at a temperature of 37° C. 1.5 ml phosphate buffer was added. 1.2 ml of the buffer was then removed from the different test tubes at different pre-determined times.

The amount of released doxycycline was determined by measuring absorption at 346 nm, using a UVIKON 933 spectrophotometer, and comparing results with a calibration curve determined by measuring solutions with known concentrations of doxycycline.

As shown in FIGS. 3A-4B, the gels prepared from solutions (FIGS. 3A and 3B) and the gels prepared from suspensions (FIGS. 4A and 4B) gradually released doxycycline, at comparable rates.

However, the total amount of doxycycline released from the gelled suspensions was considerably higher than that released from the gelled solutions, as the suspensions comprised a considerably higher concentration of doxycycline.

Example 3

Gelation of Cefdinir Suspensions and Cefdinir Release at 37° C.

Cefdinir suspensions were prepared from various concentrations of poloxamer P407, 0.1 M phosphate buffer (pH=7.0), and cefdinir, as shown in Table 3 below.

The cefdinir concentrations were in a range of 10-22.22%. In comparison, the solubility of cefdinir at 30° C. is 0.43% (w/v).

TABLE 3

Composition of prepared cefdinir suspensions

| Formulation no. | Ingredients | Amount by weight (grams) | Amount by % (% w/w) |
|---|---|---|---|
| 12 | Poloxamer P407 | 4.48 | 22.58 |
| | Phosphate buffer | 11.36 | 57.26 |
| | Cefdinir | 4.16 | 20.61 |
| 13 | Poloxamer P407 | 4.79 | 22.58 |
| | Phosphate buffer | 12.14 | 61.74 |
| | Cefdinir | 3.08 | 15.65 |
| 14 | Poloxamer P407 | 4.44 | 22.22 |
| | Phosphate buffer | 13.15 | 65.74 |
| | Cefdinir | 2.41 | 12 |
| 15 | Poloxamer P407 | 3.15 | 15.76 |
| | Phosphate buffer | 14.67 | 73.33 |
| | Cefdinir | 2.18 | 10.91 |
| 16 | Poloxamer P407 | 3.48 | 17.39 |
| | Phosphate buffer | 14.64 | 73.19 |
| | Cefdinir | 1.88 | 9.4 |
| 17 | Poloxamer P407 | 2.96 | 14.81 |
| | Phosphate buffer | 15.06 | 75.31 |
| | Cefdinir | 1.98 | 9.87 |
| 18 | Poloxamer P407 | 3.12 | 15.61 |
| | Phosphate buffer | 15.6 | 78.01 |
| | Cefdinir | 1.27 | 6.38 |
| 19 | Poloxamer P407 | 2.98 | 14.91 |
| | Phosphate buffer | 15.16 | 75.78 |
| | Cefdinir | 1.86 | 9.31 |
| 20 | Poloxamer P407 | 3.19 | 15.94 |
| | Phosphate buffer | 15.94 | 79.71 |
| | Cefdinir | 0.87 | 7.34 |
| 21 | Poloxamer P407 | 2.48 | 12.42 |
| | Phosphate buffer | 15.66 | 78.26 |
| | Cefdinir | 1.86 | 9.32 |
| 22 | Poloxamer P407 | 2.48 | 12.42 |
| | Phosphate buffer | 14.41 | 72.05 |
| | Cefdinir | 3.11 | 15.53 |
| 23 | Poloxamer P407 | 2.63 | 12.42 |
| | Phosphate buffer | 15.25 | 72.05 |
| | Cefdinir | 2.12 | 10 |

The poloxamer, buffer and active ingredient (cefdinir) were mixed using the procedures described in Example 1. Gelation of the obtained suspensions was tested as described in Example 1.

Formulations 12, 13, 15, 16, 18 and 20 gelled immediately at 37° C.

Formulation 17 gelled after 1 minute at 37° C.

Formulation 19 gelled after 60 minutes at 37° C.

Formulation 21 gelled after at least 20 minutes at 37° C.

Formulation 22 gelled after 10-12 minutes at 37° C.

These results indicate that the suspensions undergo gelation when exposed to a physiological temperature, many of them immediately upon exposure a physiological temperature.

In order to test release of cefdinir from the gelled formulations, test tubes containing 1 gram of Formulation 22 were incubated at a temperature of 37° C. 2 ml phosphate buffer (0.1 M, pH 7.0) was added after the formulation gelled. The buffer was then removed from the different test tubes at different pre-determined times.

The amount of released cefdinir was determined by HPLC (high-performance liquid chromatography), using 100 μl injection volumes, a mobile phase of 80% ammonium acetate (50 mM) solution with phosphoric acid (pH 3.0) and 20% methanol, a wavelength of 285 nm, a flow rate of 1 ml/minute, and an RP C18 column.

Figure 5:
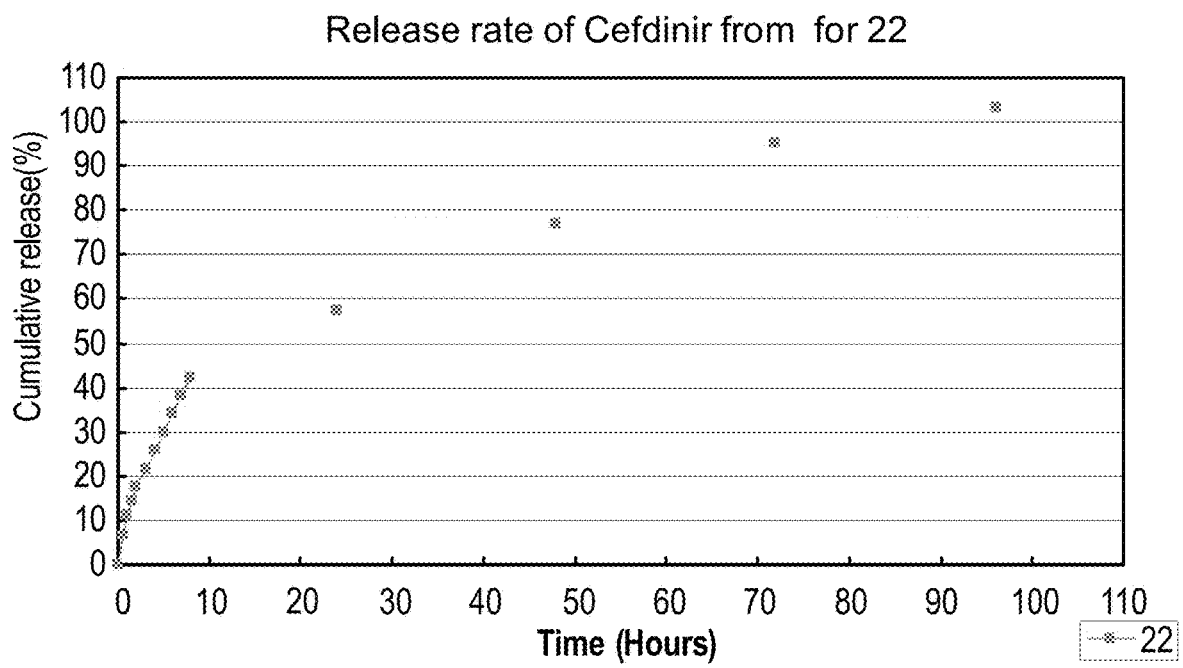
FIG. 5 presents a graph showing the release of cefdinir over time from gels prepared from a suspension comprising cefdinir, according to an exemplary embodiment of the invention.

As shown in FIG. 5, the gels prepared from the cefdinir suspension gradually released cefdinir over the course of 4 days (96 hours).

Example 4

Gelation of Enrofloxacin Suspensions and Enrofloxacin Release at 37° C.

Enrofloxacin suspensions were prepared from various concentrations of poloxamer P407, phosphate buffer (pH 6.8, according to U.S. Pharmacopeia), and enrofloxacin, as shown in Table 4 below.

The enrofloxacin concentrations were in a range of 12.05-16%. In comparison, the solubility of enrofloxacin at 25° C. is 0.25% (w/v).

TABLE 4

Composition of prepared enrofloxacin suspensions

| Formulation no. | Ingredients | Amount by weight (grams) | Amount by % (% w/w) |
|---|---|---|---|
| 24 | Poloxamer P407 | 2.48 | 12.42 |
| | Phosphate buffer | 14.41 | 72.05 |
| | Enrofloxacin | 3.11 | 16 |
| 25 | Poloxamer P407 | 2.48 | 12.42 |
| | Phosphate buffer | 15.03 | 75.16 |
| | Enrofloxacin | 3.11 | 16 |
| 26 | Poloxamer P407 | 2.42 | 12.12 |
| | Phosphate buffer | 14.91 | 74.55 |
| | Enrofloxacin | 2.67 | 13.33 |
| 27 | Poloxamer P407 | 2.87 | 14.29 |
| | Phosphate buffer | 14.67 | 72.02 |
| | Enrofloxacin | 2.63 | 13.095 |
| 28 | Poloxamer P407 | 2.65 | 13.25 |
| | Phosphate buffer | 14.71 | 73.53 |
| | Enrofloxacin | 2.65 | 13.25 |
| 29 | Poloxamer P407 | 2.65 | 13.25 |
| | Phosphate buffer | 14.94 | 74.7 |
| | Enrofloxacin | 2.41 | 12.05 |

The poloxamer, buffer and active ingredient (enrofloxacin) were mixed using the procedures described in Example 1. Gelation of the obtained suspensions was tested as described in Example 1.

Formulation 24 gelled after 1 minute at 37° C.

Formulation 25 gelled after at least 15 minutes at 37° C.

Formulation 26 gelled after at least 30 minutes at 37° C.

Formulations 27 and 28 gelled immediately at 37° C.

Formulation 29 gelled after 1-2 minutes at 37° C. However, after being kept for 2 hours at a temperature of 4° C., Formulation 29 then gelled after 8-9 minutes at 37° C.

These results indicate that the suspensions undergo gelation when exposed to a physiological temperature, many of them shortly after upon exposure a physiological temperature.

In order to test release of enrofloxacin from the gelled formulations, test tubes containing 1 gram of Formulation 29 were incubated at a temperature of 37° C. 2 ml phosphate buffer (pH 6.8) was added after the formulation gelled. The buffer was then removed from the different test tubes at different pre-determined times.

The amount of released enrofloxacin was determined by HPLC, using 100 μl injection volumes, a mobile phase of 85% phosphoric acid solution (0.1 M, pH 3.0) and 15% acetonitrile, a wavelength of 280 nm, a flow rate of 1 ml/minute, and a Hypersil BDS (base deactivated silica) 5 μm C18 column.

Figure 6:
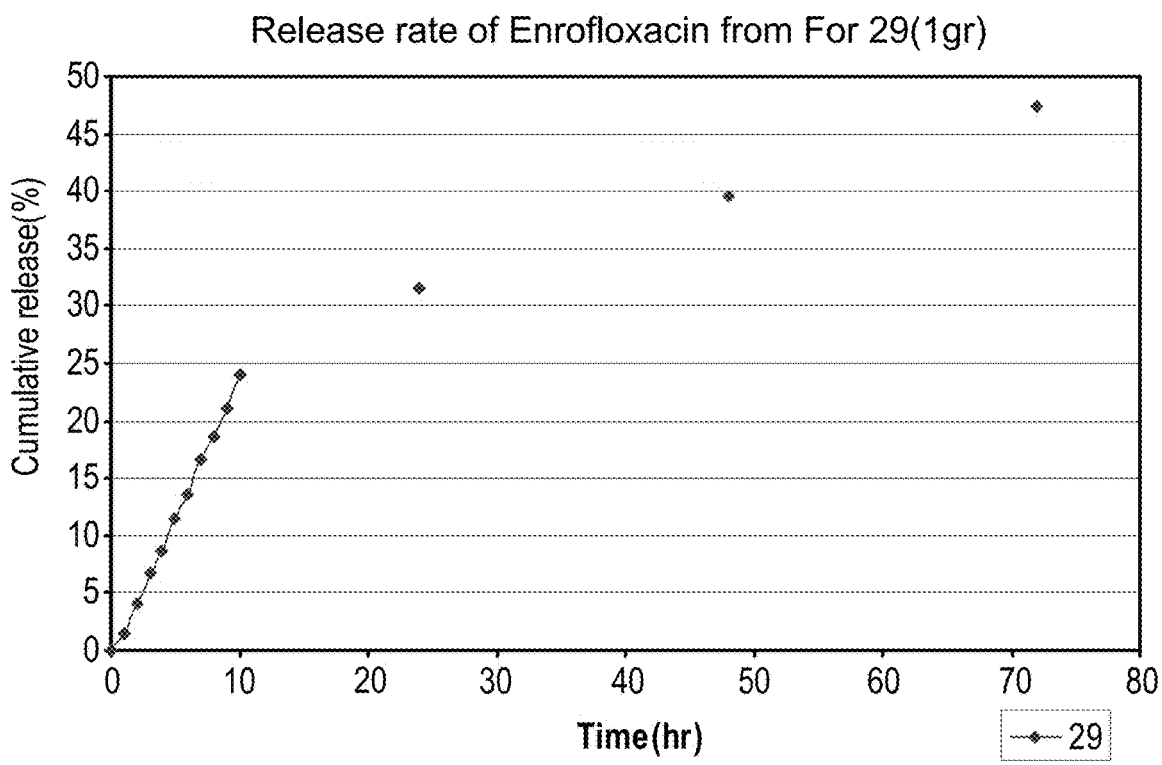
FIG. 6 presents a graph showing the release of enrofloxacin over time from gels prepared from a suspension comprising enrofloxacin, according to an exemplary embodiment of the invention.

As shown in FIG. 6, the gels prepared from the enrofloxacin suspension gradually released enrofloxacin over the course of 3 days (72 hours). Although the experiment was terminated after 3 days, less than 50% of the enrofloxacin was released by this time, indicating that the gel is capable of gradually releasing enrofloxacin for a considerably lengthier period of time.

Example 5

Amoxicillin Administration and Release in Goats

The pharmacokinetic-pharmacodynamic properties of an exemplary controlled-release amoxicillin injectable suspension were determined in vivo in Saanen goats and local goats (*Capra hircus*). Goats were held at the pen of the Robert H. Smith Faculty of Agriculture, Food and Environment, in Rehovot, Israel.

The goats used in this study serve as a model for various small and medium-sized ruminants of the Bovidae and Cervidae families such as the Fallow deer (*Dama dama*), the Nubian ibex (*Capra ibex nubiana*) and the gazelle (*Gazella gazelle*).

Eight goats (4 goats of each breed) of more than 3 years in age, during their dry season, participated in the study. The study was done using a 2×2 crossover design, i.e., each goat received two treatments. The two tested treatments were:

a) a control formulation—a commercial LA (Long Acting) injectable amoxicillin formulation (Betamox LA, Norbrook, Ireland), which is currently the best commercially available amoxicillin sustained release formulation; and b) an exemplary suspension containing 25% amoxicillin, 12% poloxamer P407 and 63% phosphate buffer (prepared as described in Example 1).

The 8 goats were divided randomly into two groups. During the first study phase, 4 goats receive the control formulation, at a dose of 15 mg/kg, by intramuscular injection 3 times every 48 hours, according the manufacturer's recommendation, while the other 4 goats received a single subcutaneous injection, at a dose of 45 mg/kg, of the exemplary amoxicillin suspension. After a wash-out period of 3 weeks, each goat received the other amoxicillin treatment during the second study phase.

During the study period, regular food rations and water were provided ad-libitum, and the goats' daily routine was uninterrupted other than for blood-drawing at the specified time periods.

Blood samples of approximately 5 ml were drawn from the jugular vein, using an aseptic procedure, 0, 1, 2, 4, 6, 8, 12, 24, 36, and 48 hours following each injection of the control formulation, and 0, 1, 2, 4, 6, 8, 12, 24, 36, 48, 60, 72, 120, 144 and 160 hours following injection of the exemplary amoxicillin suspension. All blood samples were then centrifuged at 1500 g for 8 minutes and then stored at −20° C. until being processed and analyzed.

Preparation of plasma samples was as follows: 0.05 mL of an internal standard (0.4 μg/mL cloxacillin in bi-distilled water) was added to 0.05 mL of plasma, followed by 0.1 mL of acetonitrile. The tube was centrifuged at 14000 rotations per minute for 10 minutes, 100 μL of the supernatant solution was diluted with 100 μL of bi-distilled water.

Amoxicillin was determined by use of LC/MS/MS (liquid chromatography-tandem mass spectrometry) method. The method utilized a Hewlett-Packard H-P 1100 (Agilent Technologies) liquid chromatography system (binary pump, degasser, column compartment and autosampler) combined with an Applied Biosystems API 4000 (Applied Biosystems) mass spectrometer. Liquid chromatography separation was performed on a C18 Kinetex column (2.6μ, 50×4.6 mm, Phenomenex). The mobile phase consisted of 0.2% formic acid (Merck) in bi-distilled water, and acetonitrile (J. T. Baker). A linear gradient increased acetonitrile concentration from 5% to 70% between 0 and 1 minute at a flow rate of 1.2 mL/minute. The column compartment was kept at a temperature of 30° C. and the injection volume was 2 μL. Turbo ion spray for ESI/MS/MS (electrospray ionization tandem mass spectrometry) in positive ion mode was operated at a temperature of 500° C. Multiple reaction monitoring (MRM) was applied. The precursor ion had an m/z value of 366.2 for amoxicillin and 436.2 for cloxacillin. Product ions had an m/z value of 349.1 and 114.0 for amoxicillin and 277.0 m/z for cloxacillin.

Amoxicillin and cloxacillin standards were prepared in methanol. A standard curve for plasma analysis was prepared by fortifying blank plasma with amoxicillin at concentrations in a range of from 0.025-25 μg/mL. The limit of quantification was 0.025 μg/mL and the calibration curve was linear within the range of from 0.050 to 25 μg/mL.

Plasma concentrations of amoxicillin were compared to an in vivo minimum inhibitory concentration (MIC) which was set at 0.4 μg/ml, bases on multiplication of an MIC value determined in vitro (0.1 μg/ml) by a factor of 4.

Figure 7:
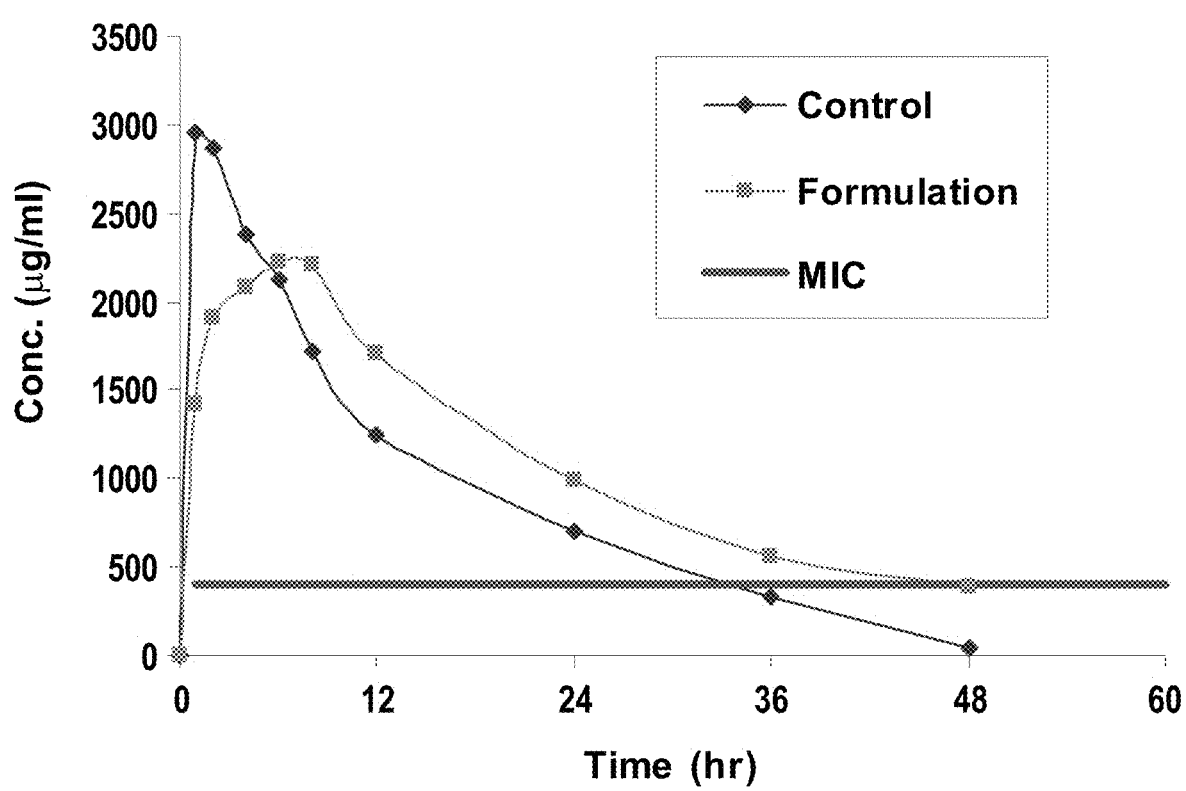
FIG. 7 presents a graph showing the plasma concentrations ($\mu g/ml$) of amoxicillin over time in goats, following injection with a suspension comprising amoxicillin, according to an exemplary embodiment of the invention (Formulation), and following injection with a commercial amoxicillin sustained release formulation (Control); a minimum inhibitory concentration (MIC) of amoxicillin is indicated for comparison.

As shown in FIG. 7, the exemplary amoxicillin suspension released amoxicillin more gradually than did the commercial sustained release formulation. Plasma concentrations of amoxicillin remained above a minimum inhibitory concentration of amoxicillin for about 48 hours after administration of the exemplary amoxicillin suspension, but for less than 36 hours after administration of the commercial formulation. As further shown therein, the peak plasma concentration upon administration of the exemplary amoxicillin suspension was lower and later than the peak plasma concentration upon administration of the commercial formulation.

These results indicate that suspensions according to embodiments of the present invention provide improved sustained release in vivo, as compared with currently available formulations.

Example 6

Amoxicillin Administration and Release in Dogs

Seven healthy beagles, weighing between 9 to 15 kg, each received a subcutaneous injection of 180 mg/kg amoxicillin in an exemplary suspension containing 25% amoxicillin, 12% poloxamer P407 and 63% phosphate buffer (prepared as described in Example 1).

Blood samples were drawn at the indicated times into heparin tubes. All blood samples were then centrifuged at 1000 g for 8 minutes, and the plasma samples were then stored at −72° C. until being processed and analyzed.

The time during which plasma concentrations remained above the minimum inhibitory concentration determined for amoxicillin in vitro (i.e., 0.1 μg/ml) was determined.

Figure 8:
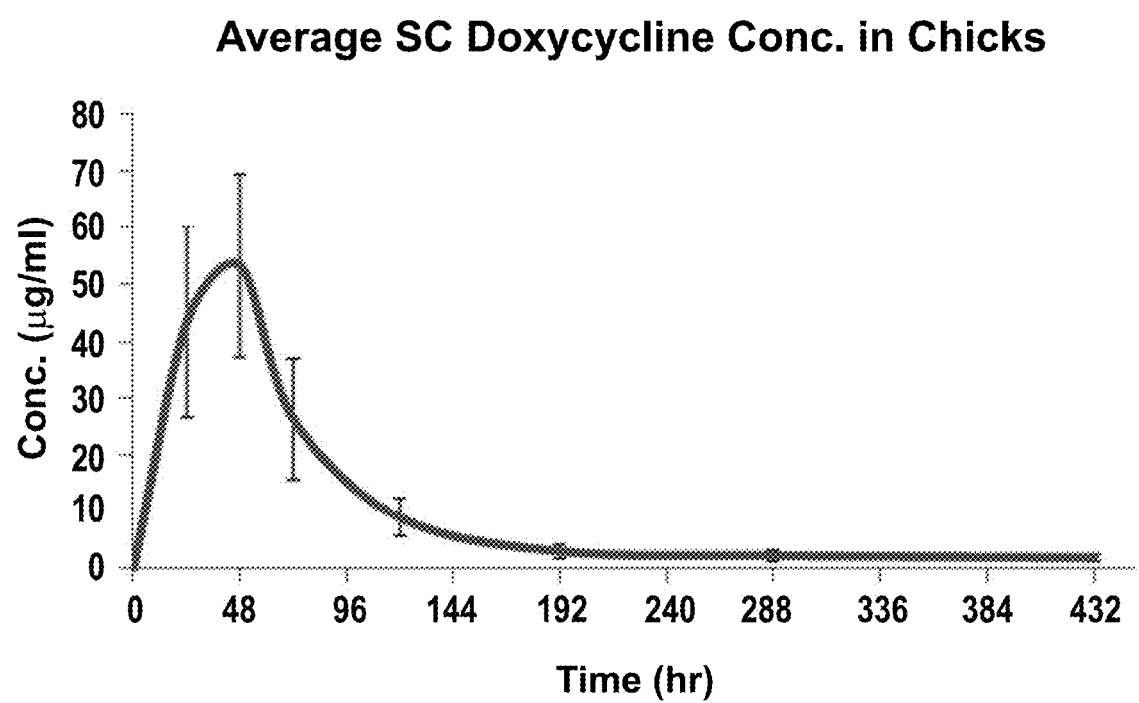
FIG. 8 presents a graph showing the plasma concentrations ($\mu g/ml$) of amoxicillin over time in beagles, following injection with a suspension comprising amoxicillin, according to an exemplary embodiment of the invention; a minimum inhibitory concentration (MIC) of amoxicillin is indicated for comparison.

As shown in FIG. 8, the plasma concentration of amoxicillin remained above the minimum inhibitory concentration of amoxicillin for about 48 hours after administration of the amoxicillin suspension.

These results further indicate that suspensions such as described herein exhibit sustained release in vivo.

Example 7

Doxycycline Administration and Release in Chicks

Chicks (n=34) received a subcutaneous injection of an exemplary suspension containing 25.8% doxycycline, 21.9% poloxamer P407 and 52.3% water (prepared as described in Example 2). Blood was drawn at the indicated times and the amount of doxycycline was measured.

Figure 9:
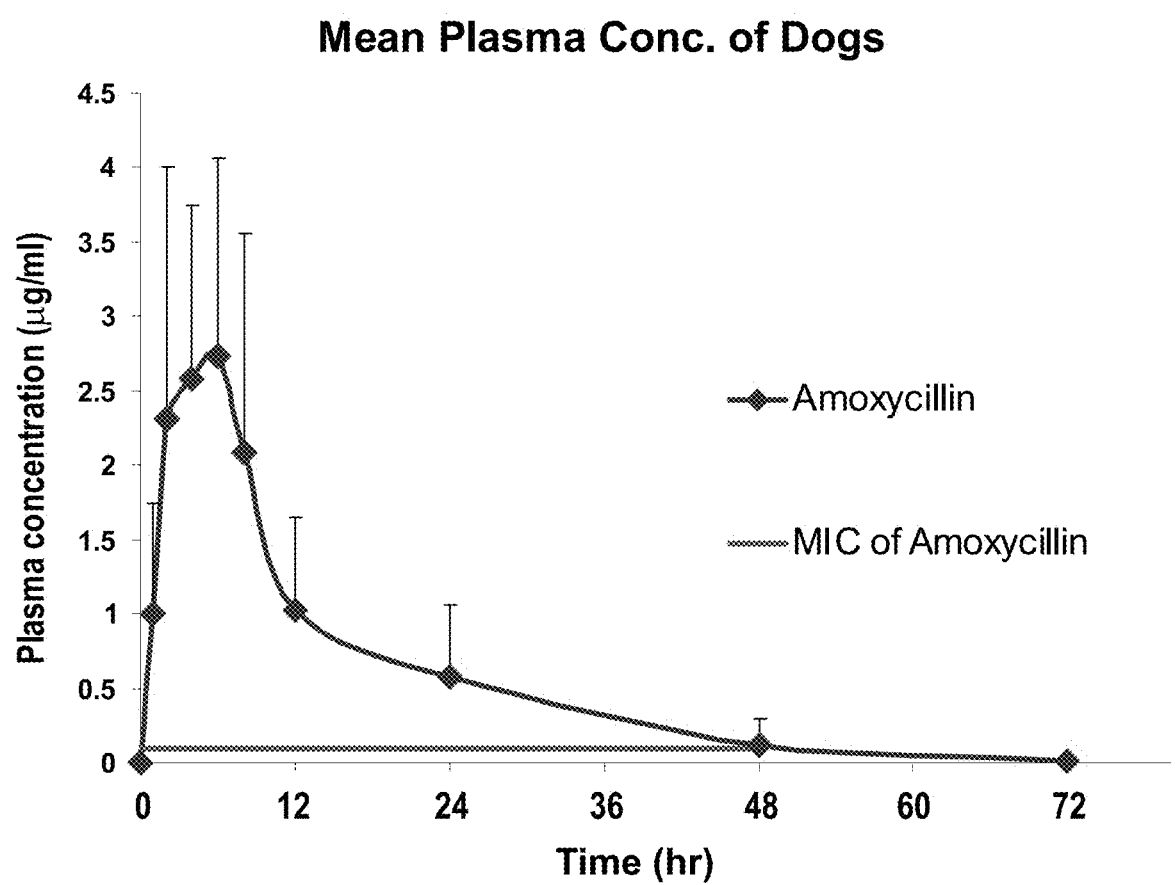
FIG. 9 presents a graph showing the plasma concentrations ($\mu g/ml$) of doxycycline over time in chicks, following injection with a suspension comprising amoxicillin, according to an exemplary embodiment of the invention.

As shown in Table 5 below and in FIG. 9, the sustained release formulation maintained therapeutic doxycycline blood concentration of over 1 μg/ml about for 18 days or longer. For *Chlamydia psittaci*, the MIC ranges from 0.05 to 0.2 μg/ml, with an average of 0.1 μg/ml. Accordingly, only two injections of the above described formulation would provide full treatment against psittacosis. The currently recommended treatment is injections of doxycycline every 5 to 7 days up to 45-60 days.

TABLE 5

Amount of doxycycline in the blood following administration of an exemplary formulation

| | | | | Avg Conc. (μg/ml) | | | | |
|---|---|---|---|---|---|---|---|---|
| | 0 | 43.9 | 53.35 | 26.35 | 8.99 | 3.05 | 2.31 | 1.93 |
| Time (hour) | 0 | 24 | 48 | 72 | 120 | 192 | 288 | 432 |
| SD* | 0 | 16.88 | 15.99 | 10.72 | 3.33 | 1.26 | 0.96 | 0.66 |

*SD = standard deviation

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An injectable composition for systemic parenteral administration to a subject in need thereof, comprising a biologically active agent having a molecular weight of less than 1000 Daltons, a polymer which exhibits reverse thermal gelation at a physiological temperature, and an aqueous carrier, wherein at least 66.67% of said biologically active agent is in an undissolved form, wherein a concentration of said biologically active agent in said composition is at least 15 weight percent, and wherein said biologically active agent is present in a concentration of less than a therapeutically effective amount per 1 milliliter.

2. The composition of claim 1, wherein said biologically active agent is a therapeutically active agent.

3. The composition of claim 1, wherein said undissolved form comprises solid particles.

4. The composition of claim 1, wherein said polymer comprises a poloxamer.

5. The composition of claim 4, wherein said poloxamer is selected from the group consisting of poloxamer 407 and poloxamer 188.

6. The composition of claim 4, wherein a concentration of said poloxamer is in a range of from 2 to 50 weight percent.

7. The composition of claim 1, wherein said biologically active agent is selected from the group consisting of an antibiotic, an antihelminthic and a hormone.

8. The composition of claim 1, wherein at least 90% of said biologically active agent is in said undissolved form.

9. The composition of claim 1, being a liquid at a temperature lower than said physiological temperature.

10. The composition of claim 9, being a gel at a physiological temperature.

11. The composition of claim 10, wherein a release of said biologically active agent from 1 ml of said gel is characterized by a half-time of at least 4 hours.

12. The composition of claim 11, wherein a release of said biologically active agent from 1 ml of said gel is characterized by a half-time in a range of from 4 hours to one week.

13. The composition of claim 1, being packaged in a packaging material and identified, in or on said packaging material, for use in the treatment of a medical condition in a subject.

14. The composition of claim 13, wherein said subject is a non-human subject.

15. The composition of claim 1, being formulated as a unit dosage form composition.

16. A kit for effecting a biological process in a subject, the kit comprising:
   (a) a biologically active agent having a molecular weight of less than 1000 Daltons;
   (b) a polymer which exhibits reverse thermal gelation at a physiological temperature; and
   (c) an aqueous carrier,
   wherein the amounts of said biologically active agent, said polymer and said aqueous carrier are such that the amount of said biologically active agent is at least 15 weight percent of the total amount of said biologically active agent, said aqueous carrier and said polymer, wherein said amount of said biologically active agent and said amount of aqueous carrier mixed with said amount of said polymer together form an injectable composition wherein at least 66.67% of said biologically active agent in said composition is in an undissolved form.

17. The kit of claim 16, further comprising instructions for mixing said biologically active agent, said polymer and said aqueous solution so as to form a composition comprising said biologically active agent in an undissolved form.

18. A kit for effecting a biological process in a subject, the kit comprising:
   (a) a biologically active agent having a molecular weight of less than 1000 Daltons;
   (b) a polymer which exhibits reverse thermal gelation at a physiological temperature;
   (c) an aqueous carrier; and,
   (d) instructions for mixing said biologically active agent, said polymer and said aqueous solution in amounts and ratio so as to form an injectable composition comprising said biologically active agent in an undissolved form, wherein a concentration of said biologically active agent in said composition is at least 15 weight percent, and wherein at least 66.67% of said biologically active agent in said composition is in said undissolved form.

19. The kit of claim 18, wherein said instructions are such that said injectable composition is formulated as a unit dosage form composition, wherein a volume of said unit dosage form composition is at least 1 ml.

20. The composition of claim 15, wherein a volume of said unit dosage form composition is at least 1 ml.

21. The composition of claim 15, wherein a volume of said unit dosage form composition is at least 2 ml.

22. An injectable composition for systemic parenteral administration to a subject in need thereof, formulated as a unit dosage form composition, wherein a volume of said unit dosage form composition is at least 1 ml, the composition comprising a biologically active agent having a molecular weight of less than 1000 Daltons, a polymer which exhibits reverse thermal gelation at a physiological temperature, and an aqueous carrier, wherein at least 66.67% of said biologically active agent is in an undissolved form, wherein a concentration of said biologically active agent in said composition is at least 5 weight percent.

23. The composition of claim 22, wherein a volume of said unit dosage form composition is at least 2 ml.

24. The composition of claim 22, wherein said biologically active agent is a therapeutically active agent.

25. The composition of claim 22, wherein said undissolved form comprises solid particles.

26. The composition of claim 22, wherein said polymer comprises a poloxamer.

27. The composition of claim 26, wherein said poloxamer is selected from the group consisting of poloxamer 407 and poloxamer 188.

28. The composition of claim 26, wherein a concentration of said poloxamer is in a range of from 2 to 50 weight percent.

29. The composition of claim 22, wherein said biologically active agent is selected from the group consisting of an antibiotic, an antihelminthic and a hormone.

30. The composition of claim 22, wherein at least 90% of said biologically active agent is in said undissolved form.

31. The composition of claim 22, wherein a concentration of said biologically active agent is at least 10 weight percent.

32. The composition of claim 22, being a liquid at a temperature lower than said physiological temperature.

33. The composition of claim 32, being a gel at a physiological temperature.

34. The composition of claim 33, wherein a release of said biologically active agent from 1 ml of said gel is characterized by a half-time of at least 4 hours.

35. The composition of claim 34, wherein a release of said biologically active agent from 1 ml of said gel is characterized by a half-time in a range of from 4 hours to one week.

36. The composition of claim 22, being packaged in a packaging material and identified, in or on said packaging material, for use in the treatment of a medical condition in a subject.

37. The composition of claim 36, wherein said subject is a non-human subject.

* * * * *